United States Patent
Wallace et al.

(10) Patent No.: US 8,314,140 B2
(45) Date of Patent: Nov. 20, 2012

(54) 4-HYDROXYTHIOBENZAMIDE DERIVATIVES OF DRUGS

(75) Inventors: John Wallace, Hamilton (CA); Giuseppe Cirino, Naples (IT); Vincenzo Santagada, Cosenza (IT); Giuseppe Caliendo, Napoli (IT)

(73) Assignee: Antibe Therapeutics Inc., Calgary (CA)

( * ) Notice: Subject to any disclaimer, the term of this patent is extended or adjusted under 35 U.S.C. 154(b) by 667 days.

(21) Appl. No.: 12/374,273

(22) PCT Filed: Jul. 18, 2007

(86) PCT No.: PCT/CA2007/001273
§ 371 (c)(1),
(2), (4) Date: Jun. 24, 2009

(87) PCT Pub. No.: WO2008/009118
PCT Pub. Date: Jan. 24, 2008

(65) Prior Publication Data
US 2009/0306412 A1    Dec. 10, 2009

Related U.S. Application Data

(63) Continuation-in-part of application No. PCT/CA2006/000484, filed on Mar. 31, 2006, and a continuation-in-part of application No. 11/759,154, filed on Jun. 6, 2007.

(60) Provisional application No. 60/807,639, filed on Jul. 18, 2006, provisional application No. 60/887,188, filed on Jan. 30, 2007, provisional application No. 60/804,067, filed on Jun. 6, 2006.

(51) Int. Cl.
*A61K 31/405* (2006.01)
*A61K 31/40* (2006.01)
*A61K 31/35* (2006.01)
*C07D 207/00* (2006.01)
*C07D 209/00* (2006.01)
*C07D 309/30* (2006.01)
*C07D 313/04* (2006.01)
*C07C 61/04* (2006.01)
*C07C 321/00* (2006.01)

(52) U.S. Cl. ........ 514/415; 514/416; 514/419; 514/451; 548/400; 548/452; 549/292; 549/293; 549/271; 562/506; 562/557

(58) Field of Classification Search ............... 560/35; 549/292, 293, 271; 562/506, 557; 548/400, 548/452; 514/415, 416, 419, 451
See application file for complete search history.

(56) References Cited

U.S. PATENT DOCUMENTS
3,338,913 A    8/1967 Yates
(Continued)

FOREIGN PATENT DOCUMENTS
WO    99/42439    8/1999
(Continued)

OTHER PUBLICATIONS

Leffler et al., "Carbamate Antimalarials", Journal of the American Chemical Society, vol. 70, No. 10, Oct. 1948, pp. 3439-3442.
(Continued)

*Primary Examiner* — Taylor Victor Oh
(74) *Attorney, Agent, or Firm* — Bennett Jones LLP

(57) ABSTRACT

Derivatives of drugs are provided, said derivatives comprising the H2S-releasing moiety 4-hydroxythiobenzamide that is either covalently linked to the drug or forms a salt with the drug. The compounds of the present invention exhibit enhanced activity or reduced side effects or both.

2 Claims, 22 Drawing Sheets

U.S. PATENT DOCUMENTS

| | | | |
|---|---|---|---|
| 4,112,095 | A | 9/1978 | Allen, Jr. et al. |
| 4,170,654 | A | 10/1979 | Stone |
| 5,214,191 | A | 5/1993 | Kirschenheuter et al. |
| 5,663,416 | A | 9/1997 | Kirschenheuter et al. |
| 6,429,223 | B1 | 8/2002 | Lai et al. |
| 7,638,513 | B2 | 12/2009 | Siddiqui et al. |
| 2006/0270635 | A1 | 11/2006 | Wallace et al. |
| 2007/0197479 | A1 | 8/2007 | Wallace et al. |

FOREIGN PATENT DOCUMENTS

| | | |
|---|---|---|
| WO | 2006100254 | 9/2006 |
| WO | WO 2006/125293 | 11/2006 |
| WO | WO 2006/125295 | 11/2006 |

OTHER PUBLICATIONS

Wang, Two's company, three's a crowd: can H2S be the third endogenous gaseous transmitter?FASEB J 2002; 16: 1792-1798.

Fiorucci et al., Inhibition of hydrogen sulfide generation contributes to gastric injury caused by anti-inflammatory nonsteroidal drugs. Gastroenterology. 2005; 129: 1210-1224.

Whiteman, M. et al., The novel neuromodulator hydrogen sulfide: an endogenous peroxynitrate 'scavenger?, J Neurochem. 2004; 90: 765-768.

Wallace et al., (1993) Am. J. Physiol. 265: 993-998.

Khan, S.U. Morris, G.F. and Hidiroglou, M. (1980) Rapid estimation of sulfide in rumen and blood with a sulfide-specific ion electrode Microchem J. 25:388-395.

Wallace et al., Cyclooxygenase 1 contributes to inflammatory responses in rats and mice: implications for gastrointestinal toxicity. Gastroenterology 1998; 115: 101-109.

Wallace et al., Limited anti-inflammatory efficacy of cyclo-oxygenase-2 inhibition in carrageenan-airpouch inflammation. Br J Pharmacol 1998; 126:1200-1204.

Zanardo et al., Hydrogen sulphide is an endogenous modulator of leukocyte-mediated inflammation. FASEB J 2006; 20: 2118-2120.

Stadler et al., Diclofenac delays healing of gastroduodenal mucosal lesions. Double-blind, placebo-controlled endoscopic study in healthy volunteers. Digestive Diseases and Sciences 1991; 35: 594-600.

Whelton, A. Nephrotoxcity of nonsteroidal anti-inflammatory drugs: physiologic foundations and clinical implications. Am. J. Med. 1999; 106 (5B): 13S-24S.

Ribeiro et al. Chronic inhibition of nitric oxide synthesis: A new model or arterial hypertension. Hypertension 1992; 20: 298-303.

Ma L., Elliott SN, Cirino G, Buret A. Ignarro L J, Wallace J L. Platelets modulate gastric ulcer healing through release of endostatin and VEGF. Proc Natl Acad Sci USA 98: 6470-6475.

Wang, G. W. et al. Novel Reactions of [60]Fullerene with Amino Acid Esters and Carbon Disulfide. J. Org. Chem. 2006. pp. 680-684. vol. 71.

Molin, J. et al. On Mechanism of Base-Catalysed Hydrolysis of Thioamides. Collection Czechoslov. Chem. Commun. 1977. pp. 517-523. vol. 42.

Molin, J. at al. Substituent and Solvent Effects in Alkaline Hydrolysis of Throamides. Collection Czechoslov. Chem. Commun. 1978. pp. 2283-2288. vol. 43.

Fiorucci, S. et al. A new Protective Mechanism in NSAID Gastropathy. Evidence that Hydrogen Sulfide (h2s) Modulates Gastric Mucosal Integrity. Annual Meeting of American Gastroenterological Association. 2005. Abstract No. 836.

4-HYDROXYTHIOBENZAMIDE DERIVATIVES OF DRUGS

This application is filed as a Continuation-in-Part of PCT/CA2006/000484, filed Mar. 31, 2006, which claims priority to PCT/CA2005/000819, filed May 27, 2005. This application is further a Continuation-in-Part of U.S. patent application Ser. No. 11/759,154, which is a Continuation-in-Part of PCT/CA2006/000484, and which claims priority to U.S. provisional patent application No. 60/804,067, filed Jun. 6, 2006. This application further claims priority to U.S. provisional patent applications Nos. 60/807,639, filed Jul. 18, 2006, and 60/887,188, filed Jan. 30, 2007.

FIELD OF INVENTION

The present invention relates to hydrogen sulfide ($H_2S$) releasing derivatives of drugs having improved activity and/or reduced side effects. In particular, the present invention relates to drug derivatives comprising the $H_2S$-releasing moiety 4-hydroxythiobenzamide either covalently linked to a drug or forming a salt with the drug.

BACKGROUND OF THE INVENTION

Nitric oxide (NO) and carbon monoxide (CO) synthesized from L-arginine by NO synthase and from heme by heme oxygenase, respectively, are the well-known neurotransmitters and are also involved in the regulation of vascular tone. Recent studies suggest that hydrogen sulfide ($H_2S$) is the third gaseous mediator in mammals. $H_2S$ is synthesized from L-cysteine by either cystathionine beta-synthase (CBS) or cystathionine gamma-lyase (CSE), both using pyridoxal 5'-phosphate (vitamin $B_6$) as a cofactor.

It is believed that $H_2S$ stimulates ATP-sensitive potassium channels ($K_{ATP}$) in the vascular smooth muscle cells, neurons, cardiomyocytes and pancreatic beta-cells. In addition, $H_2S$ may react with reactive oxygen and/or nitrogen species limiting their toxic effects but also attenuating their physiological functions, like nitric oxide does.

Recent studies have shown that $H_2S$ is involved in the regulation of vascular tone, myocardial contractility, neurotransmission, and insulin secretion. $H_2S$ deficiency was observed in various animal models of arterial and pulmonary hypertension, Alzheimer's disease, gastric mucosal injury and liver cirrhosis. It is believed that exogenous $H_2S$ ameliorates myocardial dysfunction associated with the ischemia/reperfusion injury and reduces the damage of gastric mucosa induced by anti-inflammatory drugs.

More particularly, it has recently been observed that $H_2S$ exerts anti-inflammatory and analgesic activities. $H_2S$ is an endogenous substance, produced in many tissues and affecting many functions (Wang, Two's company, three's a crowd: can $H_2S$ be the third endogenous gaseous transmitter? *FASEB J* 2002; 16: 1792-1798). It has also been shown to be a vasodilator and can suppress leukocyte adherence to the vascular endothelium (Wang, 2002; Fiorucci et al., Inhibition of hydrogen sulfide generation contributes to gastric injury caused by anti-inflammatory nonsteroidal drugs. *Gastroenterology*. 2005; 129: 1210-1224). Further, Fiorucci et al. (2005) have demonstrated that pretreatment with an $H_2S$ donor can diminish the severity of NSAID-induced gastric damage in the rat.

It is believed that the production of endogenous $H_2S$ is altered in many diseases. Furthermore, the levels of $H_2S$ may be effected by currently used drugs. For example, acetylsalic acid and non-steroidal anti-inflammatory drugs (NSAIDs) have been shown to have an inhibitory effect on the CSE-$H_2S$ pathway in gastrointestinal mucosa (Fiorucci, S. et al). This effect may contribute to gastric mucosal injury induced by these drugs. Thus, pharmacological modulation of $H_2S$ levels could be of potential therapeutic value.

It is also thought that $H_2S$ may have a role in cardiovascular pathology and, as such, its level should be examined in patients with various risk factors of atherosclerosis such as arterial hypertension, hyperlipidemia, diabetes mellitus, etc. Given that $H_2S$ is quenched by reactive oxygen species (ROS) (Whiteman, M. et al., The novel neuromodulator hydrogen sulfide: an endogenous peroxynitrate 'scavenger'?, *J. Neurochem.* 2004; 90: 765-768), and considering the important role of oxidative stress in many diseases such as atherosclerosis, arterial hypertension, Alzheimer's disease, etc., it is thought that excessive ROS production may cause $H_2S$ deficiency.

Beta-blockers, which used for angina, hypertension and cardiac arrhythmia treatment, show respiratory side effects such as dyspnoea, bronchoconstriction, etc., and therefore may cause problems in patients affected by asthma, bronchitis, and the like. Therefore, beta-blockers further worsen respiratory diseases such as asthma. Hence, in asthmatic patients doses of said drugs must be used reduced in order not to jeopardize even more the respiratory functionality. Thus the efficacy of the beta-blockers is reduced.

Antithrombotics, such as for example dipyridamole, aspirin, etc., used for the prophylaxis of thrombotic phenomena, have a number of side effects such as stomach pain, nausea and other gastrointestinal tract complications. In patients affected by pathologies connected to oxidative stress, the therapeutic action or the tolerability of these drugs, as in the case of aspirin, is greatly reduced.

Bronchodilators, for example, salbutamol, etc., are used in the treatment of asthma and bronchitis and drugs active on the cholinergic system are used in pathologies such as urinary incontinence. Their administration can produce side effects affecting the patient's cardiovascular system, causing problems both to cardiopathic and to hypertensive patients.

Expectorant and mucolytic drugs, which are used in the therapy of inflammatory states of the respiratory organs, can give rise to heartburn and gastric irritability, particularly in the elderly.

Bone resorption inhibitors, such as diphosphonates (for example alendronate, etc.) are drugs showing high gastrointestinal toxicity.

Phosphodiesterase inhibitors, such as, for example, sildenafil, zaprinast, used in the treatment of cardiovascular and respiratory system diseases, are characterized by similar problems as to tolerability and/or efficacy, in particular, in pathological conditions of oxidative stress.

Antiallergic drugs, for example, cetirizine, montelukast, etc. show similar problems in the mentioned pathological conditions, particularly with respect to their efficacy.

Anti-angiotensin drugs such as ACE-inhibitors, for example, enalapril, captopril, etc., and receptor inhibitors, for example, losartan, etc., are used in the cardiovascular disease treatment. These drugs may produce respiratory side effects (i.e., cough, etc.), in particular, in pathological conditions of oxidative stress.

Antidiabetic drugs, both of the insulin-sensitizing and of hypoglycaemizing type, such as for example sulphonylureas, tolbutamide, glypiride, glyclazide, glyburide, nicotinamide etc., are ineffective in the prophylaxis of diabetic complications. Their administration can give side effects, such as, for example, gastric lesions. These phenomena become more intense in pathological conditions of oxidative stress.

Antibiotics, for example, ampicillin, clarihtromycin, etc., and antiviral drugs, for example, acyclovir, etc., show problems as regards their tolerability, for example they cause gastro-intestinal irritability.

Antitumoral drugs, for example, doxorubicine, daunorubicin, cisplatinum, etc., have high toxicity, in a number of organs, among which are the stomach and intestines Said toxicity is further worsened in the above mentioned pathologies of oxidative stress.

Antidementia drugs, for example, nicotine and colinomimetics, are characterized by a poor tolerability especially in pathological conditions of oxidative stress.

Thus, there is a need to have available drugs showing an improved therapeutic performance, i.e., having a lower toxicity and/or higher efficacy, so that they could be administered to patients in morbid conditions of oxidative stress and/or endothelial dysfunctions, without showing the drawbacks of the drugs of the prior art.

Surprisingly, the present inventors have discovered that 4-hydroxythiobenzamide (also referred to herein as 4-HTB or TBZ) is an effective $H_2S$ releasing moiety in tissues and when either covalently linked to a drug or it forms a salt with a drug, drug derivatives are formed have reduced side effects. For example, the drug derivatives of the present invention produce significantly less gastrointestinal and/or cardiovascular side effects.

SUMMARY OF THE INVENTION

In one aspect of the present invention, derivatives of drugs are provided, said derivatives comprising the $H_2S$-releasing moiety 4-hydroxythiobenzamide (also referred to herein as 4-HTB or TBZ) that is either covalently linked to the drug or forms a salt with the drug. Surprisingly, the compounds of the present invention exhibit enhanced activity when compared to the drug alone, 4-hydroxythiobenzamide alone and the combination of the drug and 4-hydroxythiobenzamide administered separately but concomitantly or exhibit reduced side effects or both.

The compounds of the present invention produce a modest, short-lived increase in plasma $H_2S$ concentrations. Without being bound to theory, the short-lived increase in plasma $H_2S$ concentration, which is still within the physiological range, may contribute to a drugs enhanced activity, reduced gastrointestinal injury and/or reduced cardiovascular toxicity.

Further, the compounds of the present invention surprisingly induced significantly less of an increase in systolic blood pressure when administered to hypertensive rats than was observed when the drug itself was administered. A reduced propensity to elevate blood pressure may reduce the cardiovascular side effects frequently seen with prolonged use of some of the drugs.

In accordance with the present invention, there are provided compounds having the following general formula:

A-Y—X    (Formula I)

where A is a drug radical, Y is selected from the group consisting of —C(O)O—, —C(O)NH—, —C(O)OC(O)—, —C(O)NHCH$_2$C(O)—, O, S, N,

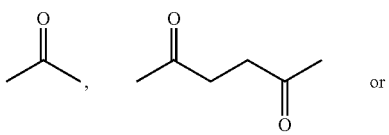

zero, and X is

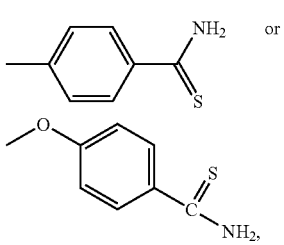

and pharmaceutically acceptable salts of the compounds, whereby when Y is zero, the drug derivative may be a salt of A and X. In a preferred embodiment, A and X are linked by means of an ester linkage, an anhydride linkage, a thioester linkage, an amide linkage or an azo linkage. In one embodiment, salts are formed with the drug radicals using thiocarbamoylbenzoate instead of 4-hydroxythiobenzamide.

The drug can be selected from a variety of known classes of drugs, including, for example, proteins, peptides, nucleotides, anti-obesity drugs, nutriceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, cardiac inotropic agents, corticosteroids, cough suppressants (expectorants and mucolytics), diuretics, dopaminergics (antiparkinsonian agents), haemostatics, immunological agents, lipid regulating agents, muscle relaxants, parasympathomimetics, parathyroid calcitonin and bisphosphonates, prostaglandins, sex hormones (including steroids), anti-allergic agents, stimulants and anoretics, sympathomimetics, thyroid agents, vasodilators and xanthines.

The following drugs are particularly useful in the present invention:

nonsteroidal anti-inflammatory drugs (NSAIDs): acetylsalicylic acid (ASA), diclofenac, naproxen, indomethacin, flurbiprofen, sulindac, ibuprofen, aceclofenac, acemetacin, benoxaprofen, benzofenac, bromfenac, bucloxic acid, butibufen, carprofen, celecoxib, cicloprofen, cinmetacin, clidenac, clopirac, diflusinal, etodolac, etoricoxib, fenbufen, fenclofenac, fenclorac, fenoprofen, fentiazac, flunoxaprofen, furaprofen, furobufen, furafenac, ibufenac, indoprofen, isoxepac, ketoprofen, ketorolac, loxoprofen, lonazolac, lumiracoxib, metiazinic, mefenamic acid, meclofenamic acid, meloxicam, nabumetone, piromidic acid, salsalate, miroprofen, oxaprozin, oxepinac, paracoxib, phenylbutazone, pirprofen, piroxicam, pirozolac, protizinic acid, rofecoxib, sodium salicylate, suprofen, tiaprofenic acid, tolmetin, valdecoxib, zomepirac, and the like;

analgesic drugs: acetaminophen, acetaminosalol, aminochlorthenoxazin, acetylsalicylic 2-amino-4-picoline acid, acetylsalicylsalicylic acid, anileridine, benoxaprofen benzylmorphine, 5-bromosalicylic acetate acid, bucetin, buprenorphine, butorphanol, capsaicine, cinchophen, ciramadol, clometacin, clonixin, codeine, desomorphine, dezocine, dihydrocodeine, dihydromorphine, dimepheptanol, dipyrocetyl, eptazocine, ethoxazene, ethylmorphine, eugenol, floctafenine, fosfosal, glafenine, hydrocodone, hydromorphone, hydroxypetidine, ibufenac, p-lactophenetide, levorphanol, meptazinol, metazocine, metopon, morphine, nalbuphine, nicomorphine, norlevorphanol, normorphine, oxycodone, oxymorphone, pentazocine, phenazocine, phenocoll, phenoperidine, phenylbutazone, phenylsalicylate, phenylramidol, salicin, salicylamide, tiorphan, tramadol, diacerein, actarit, and the like;

anticolitic drugs: 4- or 5-aminosalicylic acid, trimebutine, and the like;

respiratory and urogenital drugs (bronchodilators and drugs active on the cholinergic system, expectorants/mucolytics, antiasthmatic/antiallergic antihistaminic drugs): broncodilators and drugs active on the cholinergic system: acefylline, albuterol, bambuterol, bamifylline, bevonium methyl sulphate, bitolterol, carbuterol, clenbuterol, chlorprenaline, dioxethdrine, difylline, ephedrine, epinephrine, eproxinol, etafredine, ethylnorepinephrine, etofylline, fenoterol, flutoprium bromide, hexoprenaline, ipratropium bromide, isoetharine, isoproterenol, mabuterol, metaproterenol, oxybutynin, oxitropium bromide, pirbuterol, procaterol, protokylol, proxyphylline, reproterol, rimiterol, salmeterol, soterenol, terbutaline, 1-teobromineacetic acid, tiotropium bromide, tretoquinol, tulobuterol, zaprinast, cyclodrine, NS-21, 2-hydroxy-2,2-diphenyl-N-(1,2,3,6-tetrahydro-pyridin-4-ylmethyl)acetamide, and the like;

expectorant/mucolytic drugs: ambroxol, bromhexine, domiodol, erdosteine, guaiacol, guaifenesin, iodinated glycerol, letosteine, mesna, sobrerol, stepronin, terpin, tiopronin, and the like;

antiasthmatic/antiallergic antihistaminic drugs: acrivastine, alloclamide, amlexanox, cetirizine, clobenzepam, chromoglycate, chromolyn, epinastine, fexofenadine, formoterol, histamine, hydroxyzine, levocabastine, lodoxamide, mabuterol, montelukast, nedocromil, repirinast, seratrodast, suplatast, tosylate, terfenadine, tiaramide, urushiol, bromhexine, and the like;

ACE-inhibitors: alacepril, benazepril, captopril, ceronapril, cilazapril; delapril, enalapril, enalaprilat, fosinopril, imidapril, lisinopril, losartan, moveltipril, naphthopidil, perindopril, quinapril, ramipril, spirapril, temocapril, trandolapril, urapidil, and the like;

beta-blockers: acebutolol, alprenolol, amosulalol, arotinolol, atenolol, betaxolol, bevantolol, bucumolol, bufetolol, bufuralol, bunitrolol, bupranolol, butolfilol, carazolol, carteolol, carvedilol, celiprolol, cetamolol, dilevalol, epanolol, esmolol, indenolol, labetalol, mepindolol, metipranolol, metoprolol, moprolol, nadolol, nadoxolol, nebivolol, nifenalol, nipridalol, oxprenolol, penbutolol, pindolol, practolol, pronethalol, propranolol, sotalol, sulfinalol, talinolol, tertatolol, tilisolol, timolol, toliprolol, xibenolol, and the like;

antithrombotics and vasodilators: acetorphan, acetylsalicylic acid, argatroban, bamethan, benfurodil hemisuccinate, benziodarone, betahistine, bromvincamine, bufeniode, citicoline, clobenfurol, clopidogrel, cyclandelate, dalteparin, dipyridamol, dropenilamine, enoxaparin, fendiline, ifenprodil, iloprost, indobufen, isbogrel, isoxsuprine, heparin, lamifiban, midrodine, nadroparin, nicotinoyl alcohol, nylidrin, ozagrel, perhexyline, phenylpropanolamine, prenylamine, papveroline, reviparin sodium salt, ridogrel, suloctidil, tinofedrine, tinzaparin, triflusal, xanthinol niacinate, and the like;

antidiabetic drugs: acarbose, carbutamide, glibornuride glybuthiazol(e), miglitol, repaglinide, troglitazone, 1-butyl-3-metanyl-urea, tolrestat, nicotinamide, and the like;

antitumoral drugs: ancitabine, anthramycin, azacitidine, azaserine, 6-azauridine, bicalutamide, carubicin, carzinophilin, chlorambucil, chlorozotocin, cytarabine, daunorubicin, defosfamide, demecolcine, denopterin, 6-diazo-5-oxo-L-norleucine, docetaxel, doxifluridine, doxorubicin, droloxifene, edatrexate, eflornithine, enocitabine, epirubicin, epitiostanol, etanidazole, etoposide, fenretinide, fludarabine, fluorouracil, gemcitabine, hexestrol, idarubicin, lonidamine, mannomustine, melphalan, menogaril, 6-mercaptopurine, methotrexate, mitobronitol, mitolactol, mitomycins, mitoxantrone, mopidamol, mycophenolic acid, ninopterin, nogalamycin, paclitaxel, pentostatin, pirarubicin, piritrexim, plicamycin, podophyllic acid, porfimer sodium, porfiromycin, propagermanium, puromycin, ranimustine, retinoic acid, roquinimex, streptonigrin, streptozocin, teniposide, tenuazonic acid, thiamiprine, thioguanine, tomudex, topotecan, trimetrexate, tubercidin, ubenimex, vinblastine, vincristine, vindesine, vinorelbine, zorubicin, and the like;

antiulcer drugs: ε-acetmaidocaproic acid, arbaprostil, cetraxate, cimetidine, ecabet, enprostil, esaprazole, irsogladine, misoprostol, omeprazole, ornoprostil, pantoprazole, plaunotol, rioprostil, rosaprostol, rotraxate, sofalcone, trimoprostil, and the like;

anti-hyperlipidemic drugs (statins): atorvastatin, cilastatin, dermostatin, fluvastatin, lovastatin, mevastatin, nystatin, pentostatin, pepstatin, privastatin sodium, simvastatin, and the like;

antibiotics: amdinocillin, amoxicillin, ampicillin, apalcillin, apicycline, aspoxicillin, azidamfenicol, azidocillin, aziocillin, aztreonam, benzoylpas, benzyl penicillinic acid, biapenem, bicozamycin, capreomycin, carbenicillin, carindacillin, carumonan, cefaclor, cefadroxil, cefamandole, cetirizine, cefazedone, cefazolin, cefbuperazone, cefclidin, cefdinir, cefditoren, cefepime, cefetamet, cefixime, cefmenoxime, cefmetazole, cefminox, cefodizine, cefonicid, cefoperazone, ceforanide, cefotaxime, cefotertan, cefotiam, cefoxitin, cefozopran, cefpimizole, cefpiramide, cefpirome, cefprozil, cefroxadine, cefsulodin, ceftazidime, cefteram, ceftezole, ceftibuten, ceftiofur, ceftizoxime, ceftriaxone, cefuroxime, cefuzonam, cephacetrile sodium, cephalexin, cephaloglycin, cephaloridine, cephalosporin C, cephalothin, cephapirin sodium, cephradine, chloramphenicol, chlortetracycline, cinoxacin, clavulanic acid, clometocillin, cloxacillin, cyclacillin, cycloserine, demeclocycline, dicloxacillin, epicillin, fenbecillin, flomoxef, floxacillin, etacillin, imipenem, lenampicillin, loracarbef, lymecycline, mafenide, meclocycline, meropenem, metampicillin, methacycline, methicillin sodium, mezlocillin, minocycline, moxalactam, mupirocin, myxin, negamycin, novobiocin, oxacillin, panipenem, penicillin G potassium salt, penicillin N, penicillin O, penicillin V, phenethicillin potassium salt, pipacycline, piperacillin, pirlimycin, porfiromycin, propicillin, quinacillin, ritipenem, rolitetracycline, sancycline, sedecamycin, spectinomycin, sulbactam, sulbenicillin, temocillin, tetracycline, ticarcillin, tigemonam, tubercidin, azithromycin, clarithromycin, dirthromycin, enviomycin, erythromycin, josamycin, midecamyci, miokamycin, oleandomycin, rifabutin, rifamide, fiamycin, rifaximin, rokitamycin, spiramycin, troleandromycin, viomycin, virginiamycin; amikacin, apramycin, arbekacin, dibekacin, dihydrostreptomycin, fortimicins, gentamicin, micronomicin, neomycin, netilmicin, paromomycin, ribostamycin, sisomicin, spectinomycin, streptomicin, tobramycin, trospectromycin; bacampicillin, cefcapene pivoxil, cefpodoxime proxetil, panipenem, pivampicillin, pivcefalexin, sultamicillin, talampicillin; carbomycin, clindamycin, lincomycin, mikamycin, rosaramicin, ciprofloxacin, clinafloxacin, difloxacin, enoxacin, enrofloxacin, fleroxacin, flumequine, grepafloxacin, lomefloxacin, nadifloxacin, nalidixic acid, norfloxacin, ofloxacin, pazufloxazin, pefloxacin, pipemidic acid, piromidic acid, rufloxacin, sarfloxacin, tosulfoxain, trovafloxacin, clomocycline, guamecycline, oxytetracycline, nifurpirinol, nifurprazine; p-aminosalicyclic acid, p-aminosalicyclic acid hydrazide, clofazimine, deoxydihydrostreptomycin, ethamubtol, glyconiazide, isoniazid, opiniazide, phenyl aminosalicyclate, rifampin, rifapentine, salinazid, 4-4'-sulfynyldianiline, Acediasulfone, dapsone, succisulfone, p-sulfanilylbenzylamine, thiazolsulfone, acetyl sulfamethoxypyrazine, mafenide, 4'-(methylsulfamoyl)sulfanilanilide, salazosulfadimidine, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanole, sulfalene, sulfamerazine, sulfameter, sulfamethazine, sulfamethizole, sifamethomidine, sulfamethoxazole, sulfamethoxypyridazine, sulfamethylthiazole, sulfametrole, sulfamidochrysoidine, sulfamoxole, sulfanilamide, 2-p-sulfanilylanilinoethanol, N,4-sulfanilylsulfanilamide, sulfanilylurea, N-sulfanilyl-3,4-xylamide, sulfaperine, sulfaphenazole, sulfaproxyline, sulfapyrazine, sulfapyridine, sulfasomizole, sulfasymazine, sulfathiazole, sulfathiourea, sulfisomidine, sulfisoxazole, 4-sulfanilamido salicylic acid; negamycin, carumonan, cloxyquin, nitroxoline, arginine, metronidazole, and the like;

antiviral drugs: acyclovir, amantadine, cidofovir, cytarabine, didanosine, dideoxyadenosine, edoxudine, famciclovir, floxuridine, ganciclovir, idoxuridine, indanavir, kethoxal, lamivudine, MADU, penciclovir, podophyllotoxin, ribavirin, rimantadine, saquinavir, sorivudine, stavudine, trifluridine, valacyclovir, vidarabine, xenazoic acid, zalcitabine, zidovudine; and the like;

bone resorption inhibitors (bisphosphonates): alendronic acid, butedronic acid, etidronic acid, oxidronic acid, pamidronic acid, risedronic acid, and the like;

anti-dementia drugs: amiridine, lazabemide, mofegiline, salbeluzol, oxiracetam, ipidacrine, nebracetam, tacrine, velnacrine, and the like.

The above mentioned precursor drugs are prepared according to the methods known in the prior art. See, for example, The Merck Index, 13$^{th}$ Edition (2001), Merck & Co., Whitehouse Station, N.J., incorporated herein by reference. When available, the corresponding isomers, comprising optical isomers, can be used.

Pharmaceutical acceptable salts of the compounds of the present invention such as, for example, salts with alkaline metals and alkaline earth metals, non-toxic amines and amino acids are also part of the present invention. Preferred salts of the compounds of the present invention are the salts with arginine and agmatine. Also included are pharmaceutically acceptable acid addition salts.

The derivatives according to the invention can be used in the therapeutic indications of the precursor drug, allowing to obtain the advantages exemplified hereinafter for these drugs.

The NSAID derivatives of the present invention are very well tolerated and effective, even when the organism is debilitated and is under conditions of oxidative stress. The NSAID derivatives can be used in those pathologies wherein inflammation plays a significant pathogenetic role, such as for instance, but not limited to, in cancer, asthma, myocardic infarction.

More particularly, the NSAID derivatives of the present invention would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of the invention would be useful to treat arthritis, including but not limited to rheumatoid arthritis, spondyloarthopathies, gouty arthritis, osteoarthritis, systemic lupus erythematosus and juvenile arthritis. Such compounds of the invention would be useful in the treatment of asthma, bronchitis, menstrual cramps, tendinitis, bursitis, skin-related conditions such as psoriasis, eczema, burns and dermatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis, and for the prevention or treatment of cancer, such as colorectal cancer. Compounds of the invention would be useful in treating inflammation in such diseases as vascular diseases, migraine headaches, periarteritis nodosa, thyroiditis, aplastic anemia, Hodgkin's disease, scierodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as retinitis, retinopathies, uveitis, ocular photophobia, and of acute injury to the eye tissue. The compounds would also be useful in the treatment of pulmonary inflammation, such as that associated with viral infections and cystic fibrosis. The compounds would also be useful for the treatment or certain central nervous system disorders such as cortical dementias including Alzheimer's disease. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, atherosclerosis and central nervous system damage resulting from stroke, ischemia and trauma. The compounds would also be useful in the treatment of pain, but not limited to postoperative pain, dental pain, muscular pain, and pain resulting from cancer. Besides being useful for human treatment, these compounds are also useful for treatment of mammals, including horses, dogs, cats, rats, mice, sheep, pigs, etc.

The anticolitic drug derivatives of the present invention, for example, 4- or 5-aminosalicylic acid derivatives, trimebutine derivatives, and the like, may be utilized for the prophylaxis or treatment of various diseases, particularly inflammatory conditions of the GI tract including, but not limited to, inflammatory conditions of the mouth such as mucositis, infectious diseases (e.g., viral, bacterial and fungal diseases), and Crohn's disease; inflammatory conditions of the esophagus such as esophagitis, conditions resulting from chemical injury (e.g., lye ingestion), gastroesophageal reflux disease, bile acid reflux, Barrett's esophagus, Crohn's disease, and esophageal stricture; inflammatory conditions such as gastritis (e.g., *Helicobacter pylori*, acid-peptic disease and atrophic gastritis), celiac disease, peptic ulcer disease, pre-cancerous lesions of the stomach, non-ulcer dyspepsia, and Crohn's disease; inflammatory conditions of the stomach such as Crohn's disease, bacterial overgrowth, peptic ulcer disease, and fissures of the intestine; inflammatory conditions of the colon such as Crohn's disease, ulcerative colitis, irritable bowel syndrome, infectious colitis (e.g., pseudomembranous colitis such as *Clostridium difficile* colitis, salmonella enteritis, shigella infections, yersiniosis, cryptospiridiosis, microspridial infections, and viral infections), radiation-induced colitis, colitis in the immunocompromised host (e.g., typhlitis), precancerous conditions of the colon (e.g., dysplasia, inflammatory conditions of the bowel, and colonic polyps), proctitis, inflammation associated with hemorrhoids, proctalgia fugax, and rectal fissures; liver gallbladder and/or bilary tract conditions such as cholangitis, sclerosing cholangitis, primary bilary cirrhosis, and cholecystitis; and intestinal abscess.

Statins are used for preventing and treating atherosclerosis that causes chest pain, heart attacks, strokes, and intermittent claudication in individuals who have or are at risk for atherosclerosis. Risk factors for atherosclerosis include abnormally elevated cholesterol levels, a family history of heart attacks (particularly at a young age), increasing age, and diabetes. Most individuals are placed on statins because of high levels of cholesterol. Though cholesterol reduction is important, heart disease is complex and other factors such as inflammation may play a role. It is known, however, that statins exhibit adverse effects such as, for example, hepatopathy, possible carcinogenic potential, muscular side effects and myopathy.

The statin derivatives of the present invention may reduce the side effects associated with statins and/or have improved pharmacological activity. Surprisingly, the simvastatin derivative, succinic acid 2-{2-[8-(2,2-dimethyl-butyryloxy)-2,6-dimethyl-1,2,6,7,8,8a-hexahydro-naphthalen-1-yl]-ethyl}-6-oxo-tetrahydro-pyran-4-yl ester 4-thiocarbamoyl-phenyl ester, significantly reduced platelet aggregation at concentrations of 3, 10 and 30 μM when compared to the corresponding statin alone. Further, the simvastatin derivative of the present invention caused a significant increase in platelet cAMP when compared to the same concentrations of simvastatin alone.

The adrenergic blockers, either α- or β-blockers, derivatives of the present invention may be utilized for the prophylaxis or treatment of hypertension, angina, mitral valve prolapse, congestive heart failure, myocardial infarction, glaucoma, migraine headaches, tachycardia, and tremors, with reduced side effects.

The antithrombotic drug derivatives, for example, the aspirin derivatives, of the present invention, potentiate antiplatelet activity with improved gastric tolerability. The principal indications of antithrombotic drugs are the prevention and treatment of venous thromboembolism (VTE), the prevention of stroke in patients with atrial fibrillation and the prevention and treatment of acute coronary syndrome (ACS).

The bronchodilator derivatives and derivatives of drugs active on the cholinergic system are useful in relieving asthma symptoms by relaxing the muscle bands that tighten around the airways. In short-acting forms, bronchodilator derivatives relieve or stop asthma symptoms and are very helpful during an asthma attack. In long-acting forms, bronchodilator derivatives help control asthma symptoms and prevent asthma attacks. The present derivatives lower the side effects affecting the cardio-vascular system such as tachycardia, hypertension, etc.

The expectorants and mucolytic drugs derivatives of the present invention are useful in the loosening and clearing of mucus and phlegm from the respiratory tract. The gastrointestinal tolerability of the expectorants and mucolytic drugs may be improved when derivatized with 4-hydroxythiobenzamide as disclosed in the present invention.

Bisphosphonate derivatives of the present invention are useful in the treatment or prophylaxis of calcium metabolism disturbances or disease, for example, osteoporosis, Bechterew's disease, bone metastases, urolithiasis, heterotropic ossifications, rheumatoid arthritis osteoarthritis or degenerative arthrosis. The toxicity relating to the gastrointestinal tract may be lowered in the derivatives of the present invention.

The therapeutic efficacy of the phosphodiesterase (PDE) inhibitors (bronchodilators) derivatives of the present invention is improved and the side effects reduced. PDE inhibitors have proven potential as anti-inflammatory drugs especially in airway diseases. They suppress the release of inflammatory signals, e.g., cytokines, and inhibit the production of reactive oxygen species. PDE inhibitors have a high therapeutic and commercial potential as non-steroidal disease controllers in inflammatory airway diseases such as asthma, COPD and rhinitis.

Better efficacy and/or lower side effects may also be observed for derivatives of anti leukotrienic drugs, ACE inhibitors, antidiabetic drugs, antibiotic, antiviral and antitumoral drugs.

Compounds of the present invention can be prepared as follows:

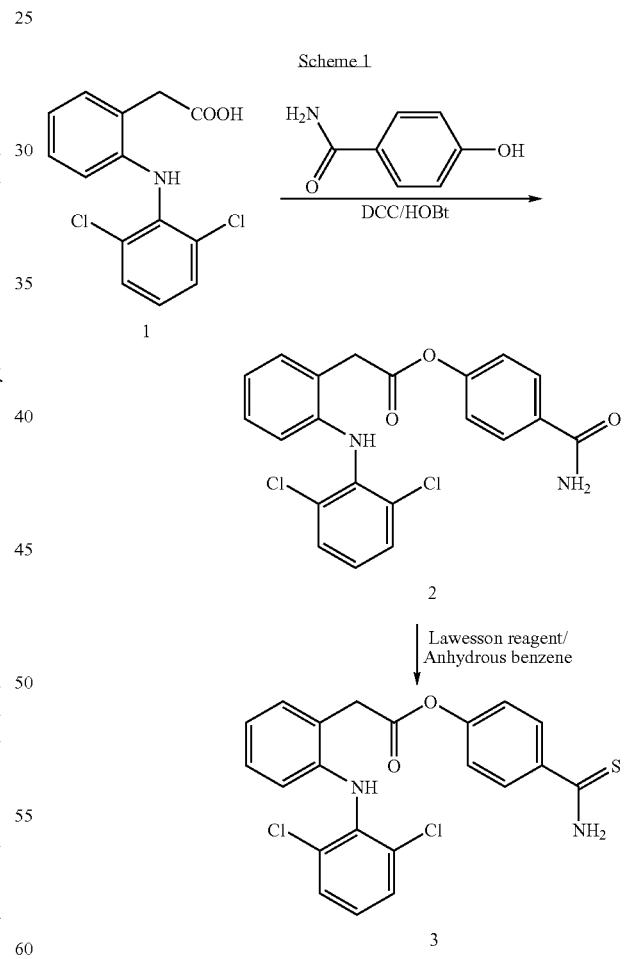

Scheme 1 is shown below using as an example the synthesis of the NSAID derivative, [2-(2,6-dichloro-phenylamino)-phenyl]-acetic acid 4-thiocarbamoyl-phenyl ester. In this scheme, Lawesson reagent is used to add a sulfur group to the hydrogen sulfide releasing moiety after it is covalently bound to the NSAID.

Diclofenac (1), which has a free carboxyl group, is first dissolved in dimethylformamide, and hydroxybenzotriazole (HOBt) and 1,3-dicyclohexylcarbodiimide (DCC) are added. To this mixture is added 4-hydroxybenzamide under conditions suitable to form a precursor (e.g., 4-carbamoylphenyl 2-(2-(2,6-dichlorophenylamino)phenyl)acetate (2)) of a compound of the present invention, which precursor lacks a sulfur. A suitable compound which can add a sulfur group such as Lawesson reagent is added to form a compound of the present invention (e.g., [2-(2,6-dichloro-phenylamino)-phenyl]-acetic acid 4-thiocarbamoyl-phenyl ester (3)).

Depending on the specific condition or disease state to be treated, subjects may be administered compounds of the present invention at any suitable therapeutically effective and safe dosage, as may be readily determined within the skill of the art. These compounds are, most desirably, administered in dosages ranging from about 1 to about 2000 mg per day, in single or divided doses, although variations will necessarily occur depending upon the weight and condition of the subject being treated and the particular route of administration chosen. It is understood that dosages will be affected by the particular drug used to form the compounds of the present invention. However, a dosage level that is in the range of about 0.1 to about 100 mg/kg, preferably between about 5 and 90 mg/kg, and more preferably between about 5 and 50 mg/kg, is most desirable. Variations may nevertheless occur depending upon the weight and conditions of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such large doses are first divided into several small doses for administration throughout the day.

The compounds of the present invention can be administered in the form of any pharmaceutical formulation, the nature of which will depend upon the route of administration. These pharmaceutical compositions can be prepared by conventional methods, using compatible, pharmaceutically acceptable excipients or vehicles. Examples of such compositions include capsules, tablets, transdermal patches, lozenges, troches, sprays, syrups, powders, granulates, gels, elixirs, suppositories, and the like, for the preparation of extemporaneous solutions, injectable preparations, rectal, nasal, ocular, vaginal etc. A preferred route of administration is the oral and rectal route.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with sweetening or flavoring agents, coloring matter and, if so desired, emulsifying and/or suspending agents, together with such diluents as water, ethanol, propylene glycol, glycerin and various combinations thereof.

The dosage form can be designed for immediate release, controlled release, extended release, delayed release or targeted delayed release. The definitions of these terms are known to those skilled in the art. Furthermore, the dosage form release profile can be effected by a polymeric mixture composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. The aqueous solutions are suitable for intravenous injection purposes. The preparation of all these solutions under sterile conditions is readily accomplished by standard pharmaceutical techniques well known to those skilled in the art.

The following examples further describe and enable a person ordinarily skilled in the art to make and use the invention. It should be appreciated however that these embodiments are for the purpose of illustrating the invention, and are not to be construed as limiting the scope of the invention as defined by the claims.

DETAILED DESCRIPTION OF THE INVENTION

Preparation of Compounds

Figure 1:
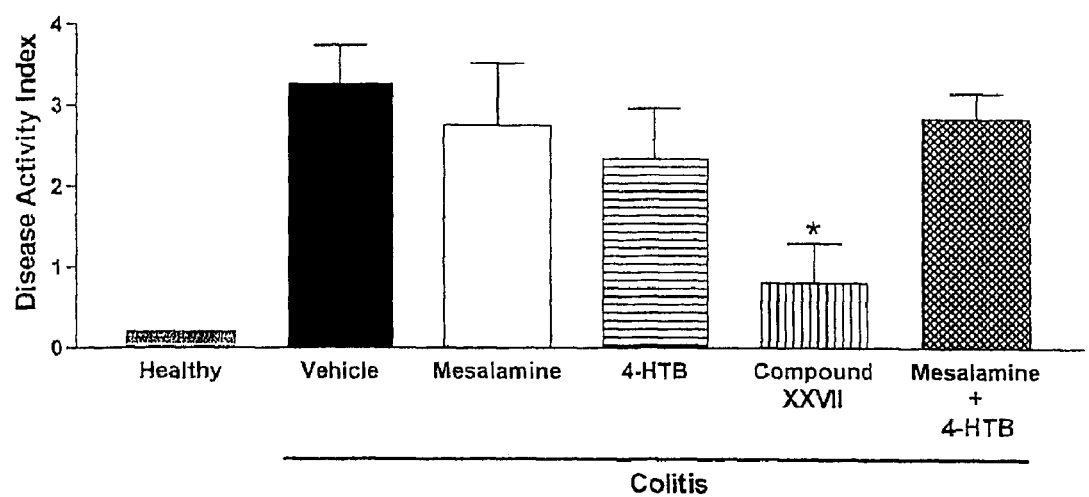
FIG. 1 shows the Disease Activity Score of mice having TNBS-induced colitis after treatment with 5-amino-2-(4-thiocarbamoyl-phenoxycarbonyloxy)-benzoic acid (Compound XXVII), mesalamine alone, 4-hydroxythiobenzamide (4-HTB) alone and a mixture of mesalamine and 4-HTB.

Thin layer chromatography was performed on Macherey-Nagel silica gel 50 plates with fluorescent indicator and the plates were visualized with UV light (254 nm). Kieselgel 60 was used for column chromatography. All synthetic reagents were purchased from the Aldrich-Sigma Chemical Company and were used without purification. Solvents were analytical reagent grade or higher purity and were used as supplied. A Buchi R-114 rotavapor was utilized for the removal of the solvents in vacuo. The structures were verified spectroscopically by proton $^1$H-NMR and $^{13}$C-NMR. Spectra were recorded on Varian Mercury Plus 400 instrument. Chemical shifts are referred to $Me_4Si$ as internal standard. Mass spectra of the synthesized products were performed on Applied Biosystem API 2000 mass spectrometry. Melting point was performed on Buchi B-540 instrument. The purity of the final compound was determined by RP-HPLC. The column was connected to Rheodyne model 7725 injector, a Waters 600 HPLC system, a Waters 486 tunable absorbance detector set to 215 or 235 nm and a Waters 746 chart recorder. The synthesized compounds gave satisfactory elemental analyses; where analyses are indicated only by the symbols of the elements, results are within ±0.4% of theoretical values.

Example 1

Synthesis of [2-(2,6-dichloro-phenylamino)-phenyl]-acetic acid 4-thiocarbamoyl-phenyl ester (also referred to as Compound XVII)

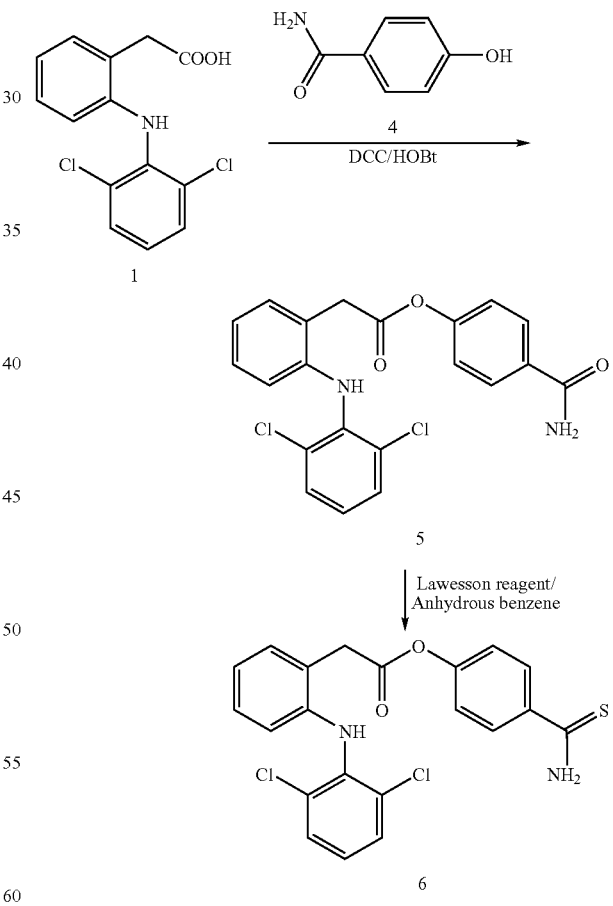

Synthesis of 4-carbamoylphenyl 2-[2-(2,6-dichlorophenylamino)-phenyl]acetate (5)

To the solution of 1 (diclofenac, 890 mg, 3.0 mmol) in 50 mL of N,N-dimethylformamide, hydroxybenzotriazole (445 mg, 3.3 mmol) and DCC (680 mg, 3.3 mmol) were added with stirring at 0° C. for 1 h. To the reaction mixture 4-hydroxybenzamide (4, 616 mg, 4.5 mmol) was added and stirred for 1 h at 0° C. and 3 hs at room temperature. After filtration, the filtrate was evaporated under reduced pressure and the oily residue thus obtained was dissolved in chloroform; the organic layer was washed with brine, dried on anhydrous MgSO$_4$, filtered and the solvent evaporated. The crude product 5 was loaded on a silica gel open column and eluted with CH$_2$Cl$_2$/MeOH (9/1), from which 4-carbamoylphenyl 2-(2-(2,6-dichlorophenylamino)phenyl)acetate (5) was obtained (212 mg, 17% yield).

Synthesis of [2-(2,6-dichloro-phenylamino)-phenyl]-acetic acid 4-thiocarbamoyl-phenyl ester (6)

4-Carboxylphenyl 2-(2-(2,6-dichlorophenylamino)phenyl)acetate (5, 480 mg, 1.14 mmol) and Lawesson reagent (460 mg, 1.14 mmol) were dissolved in 20 ml of anhydrous benzene. The reaction was warmed to 50° C. and stirred for 6 h. The solvent was removed under reduced pressure; the crude residue was purified by silica gel column (dichloromethane/methyl alcohol 9.5/0.5) to furnish the pure compound 6 (446 mg, 91% yield).

$^1$H NMR (CDCl$_3$): δ 4.07 (s, 2H), 6.59 (d, 1H), 6.67 (s, 1H), 6.98 (t, 1H), 7.14 (t, 1H), 7.19 (d, 1H), 7.28 (t, 1H), 7.33 (d, 2H), 7.63 (s, 1H), 7.97 (d, 2H);

$^{13}$C NMR (DMSO-d$_6$): δ38.8, 118.8, 121.8, 122.6, 123.7, 124.4, 128.7, 129.1, 129.6, 131.2, 137.2, 137.8, 142.9, 153.5, 170.5, 193.2, 201.7

MS (EI), m/e 431 (M$^+$);
m.p.: 170-172° C.

Example 2

Synthesis of 4-thiocarbamoylphenyl 2-(2-(2-chloro-6-fluorophenylamino)-5-methylphenyl)acetate (also referred to as Compound XVIII)

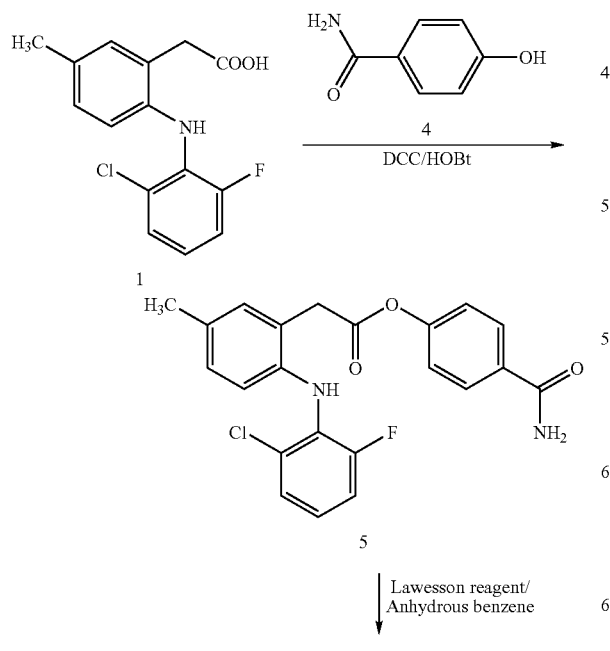

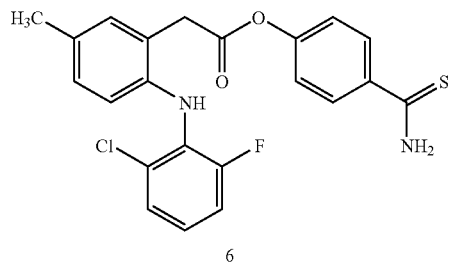

Synthesis of 4-carbamoylphenyl-2-(2-(2-chloro-6-fluorophenylamino)-5-methylphenyl)acetate (5)

To the solution of 1 (lumiracoxib, 223 mg, 0.75 mmol) in 15 mL of dimethylformamide, hydroxybenzotriazole (111 mg, 0.825 mmol) and DCC (170 mg, 0.825 mmol) were added with stirring at 0° C. for 1 h. To the reaction mixture 4-hydroxybenzamide (4, 154 mg, 1.125 mmol) was added and stirred for 1 h at 0° C. and 3 h at room temperature. After filtration, the filtrate was evaporated under reduced pressure to remove the solvent. The oily residue thus obtained was dissolved in chloroform; the organic layer was washed with brine, dried on anhydrous MgSO$_4$, filtered and the solvent evaporated. The crude product 5 was loaded on a silica gel open column and eluted with CH$_2$Cl$_2$/MeOH (9/1), from which 4-carbamoylphenyl-2-(2-(2-chloro-6-fluorophenylamino)-5-methylphenyl)acetate (5) was obtained (111 mg, 35% yield).

Synthesis of 4-thiocarbamoylphenyl-2-(2-(2-chloro-6-fluorophenylamino)-5-methylphenyl)acetate (6)

4-Carbamoylphenyl-2-(2-(2-chloro-6-fluorophenylamino)-5-methylphenyl)acetate, 5 (110 mg, 0.27 mmol) and Lawesson reagent (109 mg, 0.27 mmol) were dissolved in 15 ml of anhydrous benzene. The reaction was warmed to 60° C. and stirred for 3 h. The solvent was removed under reduced pressure; the crude residue was purified by silica gel column (dichloromethane/methyl alcohol 9.5:0.5) to furnish the pure compound 6 (59 mg, 51% yield).

$^1$H NMR (CDCl$_3$): δ 2.32 (s, 3H), 4.01 (s, 2H), 6.46 (s, 1H), 6.70 (d, 1H), 6.92 (t, 1H), 7.01 (d, 2H), 7.11 (d, 2H), 7.19 (d, 1H), 7.62 (s, NH), 7.84 (d, 2H);

$^{13}$C NMR (DMSO-d$_6$): δ20.8, 30.7, 115.1, 119.2, 122.0, 122.3, 124.1, 124.9, 126.1, 128.2, 129.2, 132.3, 134.8, 138.6, 140.9, 153.7, 154.6, 156.2, 170.4, 201.7

MS (EI), m/e 429 (M$^+$);
m.p.: 120-122° C.

Example 3

Synthesis of 2-Acetoxy-benzoic acid 4-thiocarbamoyl-pheny ester (also referred to as Compound XVI)

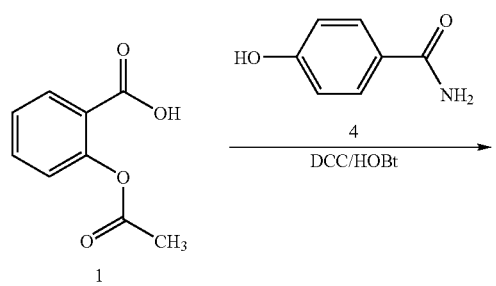

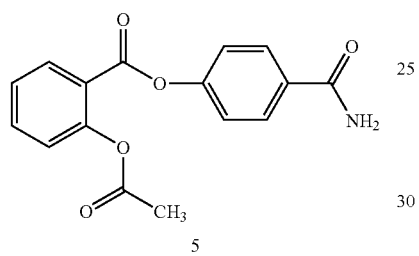

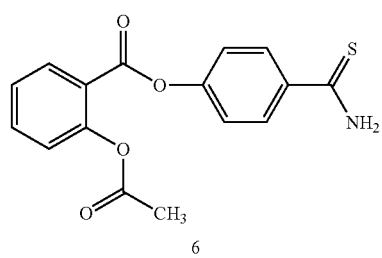

Synthesis of 4-carbamoylphenyl 2-acetoxybenzoate (5)

To the solution of 1 (acetylsalicylic acid, 500 mg, 2.77 mmol) in 15 mL of dimethylformamide, hydroxybenzotriazole (412 mg, 3.05 mmol) and DCC (628 mg, 3.05 mmol) were added with stirring at 0° C. for 1 h. To the reaction mixture 4-hydroxybenzamide (4, 418 mg, 3.05 mmol) was added and stirred for 1 h at 0° C. and 3 h at room temperature. After filtration, the filtrate was evaporated under reduced pressure to remove the solvent. The oily residue thus obtained was dissolved in chloroform; the organic layer was washed with brine, dried on anhydrous $MgSO_4$, filtered and the solvent evaporated. The crude product 5 was loaded on a silica gel open column and eluted with $CH_2Cl_2$/MeOH (9/1), from which 4-carbamoylphenyl 2-acetoxybenzoate (5) was obtained (410 mg, 47% yield).

Synthesis of 4-thiocarbamoylphenyl-2-(2-(2-chloro-6-fluorophenylamino)-5-methylphenyl)acetate (6)

4-Carbamoylphenyl 2-acetoxybenzoate, 5 (410 mg, 1.37 mmol) and Lawesson reagent (554 mg, 1.37 mmol) were dissolved in 35 ml of anhydrous benzene. The reaction was warmed to 60° C. and stirred for 3 h. The solvent was removed under reduced pressure; the crude residue was purified by silica gel column (dichloromethane/methyl alcohol 9.5:0.5) to furnish 470 mg of crude compound 6. The obtained compound was purified by preparative RP-HPLC carried out by two solvent systems: A: 100% acetonitrile in 0.1% TFA, B: 100% $H_2O$ in 0.1% TFA (linear gradient from 10% A to 60% A over 35 min, UV detection at 254 nm, flow rate 30 mL/min) giving the pure compound 6 (324 mg, 71% yield).

$^1$H NMR ($CDCl_3$): δ 2.30 (s, 3H), 7.17 (d, 1H), 7.21 (d, 2H), 7.40 (t, 1H), 7.66 (t, 1H), 7.94 (d, 2H), 8.2 (d, 1H).

$^{13}$C NMR (DMSO-$d_6$): δ21.2, 121.9, 122.4, 124.3, 126.4, 128.7, 132.4, 135.1, 137.3, 151.5, 153.7, 162.7, 169.8, 201.8

MS (EI), m/e 316 ($M^+$);

m.p.: 154-156° C.

Example 4

Synthesis of [1-(4-Chloro-benzoyl)-5-methoxy-2-methyl-1-H-indol-3-yl]-acetic acid 4-thiocarbamoyl-phenyl ester (also referred to as Compound XIX)

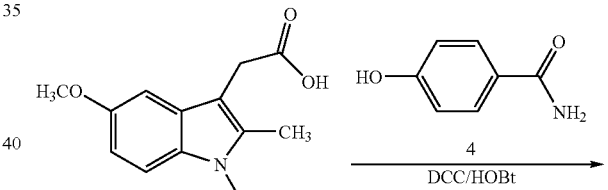

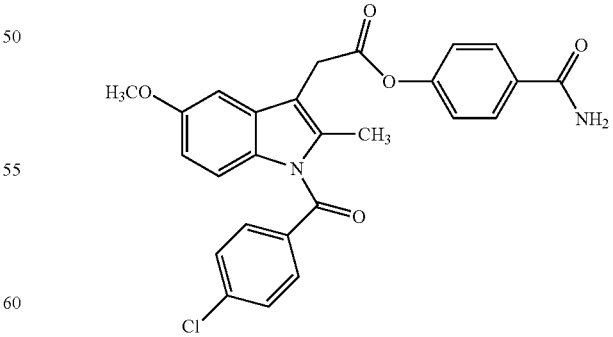

-continued

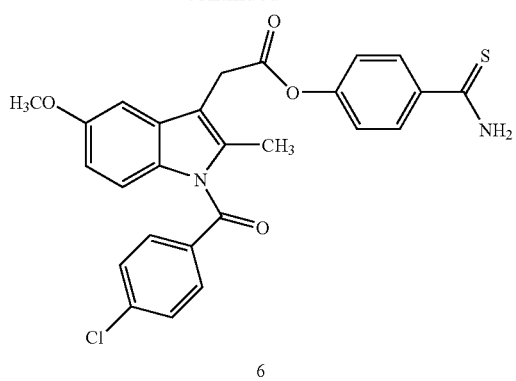

6

Synthesis of 4-carbamoylphenyl-2-[1-(4-chlorobenzoyl)-5-methoxy-2-methyl-indol-3-yl]-acetate (5)

To the solution of 1 (indomethacin, 3 g, 8.38 mmol) in 60 mL of dimethylformamide, hydroxybenzotriazole (1.25 g, 9.22 mmol) and DCC (1.9 g, 9.22 mmol) were added with stirring at 0° C. for 1 h. To the reaction mixture 4-hydroxybenzamide (4, 1.72 g, 12.6 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with NaHCO$_3$ 5%, with citric acid 10% and than dried on anhydrous MgSO$_4$, filtered and the solvent evaporated. The crude product 5 was loaded on a silica gel open column and eluted with CH$_2$Cl$_2$/MeOH (9.5/0.5), from which 4-carbamoylphenyl-2-[1-(4-chlorobenzoyl)-5-methoxy-2-methyl-indol-3-yl]-acetate (5) was obtained (479 mg, 12% yield).

Synthesis of 4-thiocarbamoylphenyl-2-[1-(4-chlorobenzoyl)-5-methoxy-2-methyl-indol-3-yl]-acetate (6)

4-carbamoylphenyl-2-[1-(4-chlorobenzoyl)-5-methoxy-2-methyl-indol-3-yl]-acetate, 5 (340 mg, 0.71 mmol) and Lawesson reagent (287 mg, 0.71 mmol) were dissolved in 15 ml of anhydrous benzene. The reaction was warmed to 60° C. and stirred for 4 h. The solvent was removed under reduced pressure; the crude residue was purified by silica gel column (dichloromethane/methyl alcohol 9.5:0.5) to furnish 178 mg of crude compound 6. The obtained compound was purified by preparative RP-HPLC carried out by two solvent systems: A: 100% acetonitrile in 0.1% TFA, B: 100% H$_2$O in 0.1% TFA (linear gradient from 10% A to 80% A over 30 min, UV detection at 254 nm, flow rate 30 mL/min) giving the pure compound 6 (56 mg, 16% yield).

$^1$H NMR (CDCl$_3$): δ 2.45 (s, 3H), 3.83 (s, 3H, OCH$_3$), 3.91 (s, 2H), 6.70 (d, 1H), 6.88 (d, 1H), 7.04 (s, 1H), 7.11 (d, 2H), 7.47 (d, 2H), 7.67 (d, 2H), 7.88 (d, 2H).

$^{13}$C NMR (DMSO-d$_6$): δ13.6, 30.8, 56.0, 101.5, 111.9, 112.0, 115.3, 121.7, 128.6, 129.4, 130.8, 131.2, 131.4, 134.0, 136.8, 137.1, 139.7, 156.2, 157.9, 167.6, 169.8, 201.8

MS (EI), m/e 493 (M$^+$);

m.p.: 224-226° C.

Example 5

Synthesis of 2-(6-Methoxy-naphthalen-2-yl)-propionic acid 4-thiocarbamyl-phenyl ester (also referred to as Compound XX)

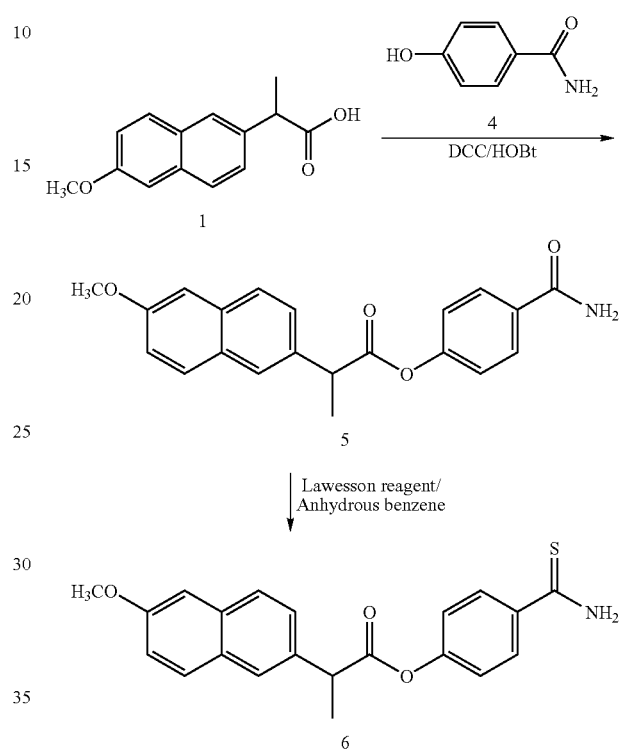

Synthesis of 4-carbamoylphenyl 2-(2-methoxynaphthalen-6-yl)propanoate (5)

To the solution of 1 (naproxen, 4 g, 17.4 mmol) in 80 mL of dimethylformamide, hydroxybenzotriazole (2.59 g, 19.14 mmol) and DCC (2.59 g, 19.14 mmol) were added with stirring at 0° C. for 1 h. To the reaction mixture 4-hydroxybenzamide (4, 3.58 g, 26.1 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with NaHCO$_3$ 5%, with citric acid 10% and than dried on anhydrous MgSO$_4$, filtered and the solvent evaporated. The crude product 5 was loaded on a silica gel open column and eluted with CH$_2$Cl$_2$/MeOH (9.5/0.5), from which 4-carbamoylphenyl 2-(2-methoxynaphthalen-6-yl)-propanoate (5) was obtained (1.91 g, 32% yield).

Synthesis of 4-thiocarbamoylphenyl 2-(2-methoxynaphthalen-6-yl)propanoate (6)

4-Carbamoylphenyl 2-(2-methoxynaphthalen-6-yl)-propanoate, 5 (1.80 g, 4.34 mmol) and Lawesson reagent (1.75 g, 4.34 mmol) were dissolved in 130 ml of anhydrous benzene. The reaction was warmed to 60° C. and stirred for 4 h. The solvent was removed under reduced pressure; the crude residue was purified by silica gel column (dichloromethane/methyl alcohol 9.75:0.25) to furnish 2.9 g of crude compound 6. The obtained compound was purified by a silica gel open column and eluted with CH$_2$Cl$_2$/MeOH (9.5/0.5)) giving the pure compound 6 (970 mg, 61% yield).

$^1$H NMR (DMSO-d$_6$): δ 1.59 (d, 3H), 3.86 (s, 3H, OCH$_3$), 4.24 (dd, 1H), 7.06 (d, 2H), 7.18 (d, 1H), 7.31 (s, 1H), 7.50 (d, 1H), 7.84 (s, 1H) 7.85 (d, 1H), 7.86 (s, 1H), 7.89 (d, 2H), 9.47 and 9.84 (s, 2H, NH$_2$).

$^{13}$C NMR (DMSO-d$_6$): δ 19.1, 45.2, 55.9, 106.5, 119.6, 121.6, 126.6, 126.9, 128.0, 129.4, 129.9, 134.2, 135.6, 137.8, 153.4, 158.1, 173.3, 199.7.

MS (EI), m/e 366 (M$^+$);
m.p.: 196-198° C.

Example 6

Synthesis of 4-thiocarbamoylphenyl 2-(4-isobutylphenyl)propanoate

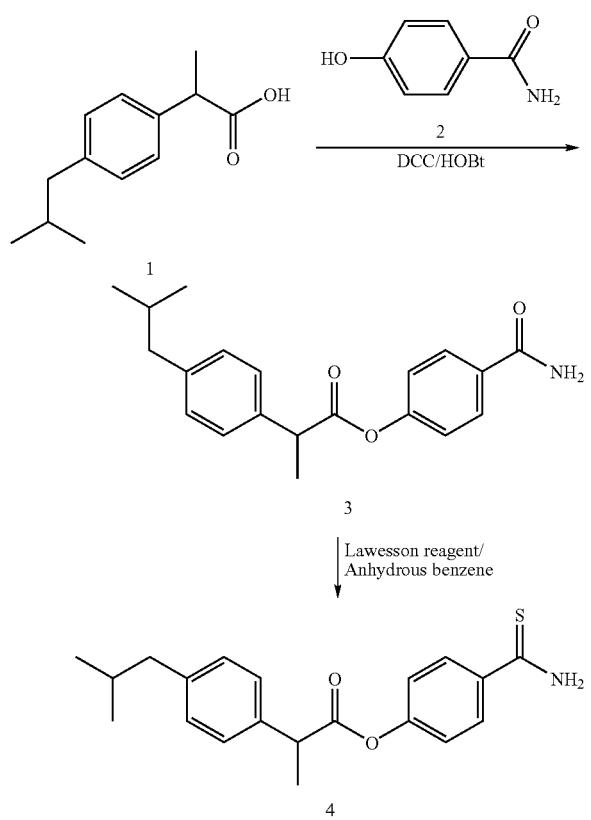

To the solution of 1 (ibuprofen, 3.87 g, 18.8 mmol) in 80 mL of dimethylformamide, hydroxybenzotriazole (2.8 g, 20.7 mmol) and DCC (4.27 g, 20.7 mmol) were added with stirring at 0° C. for 1 h. To the reaction mixture 4-hydroxybenzamide (2, 3.9 g, 28 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with NaHCO$_3$ 5%, with citric acid 10% and than dried on anhydrous MgSO$_4$, filtered and the solvent evaporated. The crude product 3 was loaded on a silica gel open column and eluted with CH$_2$Cl$_2$/MeOH (9.5/0.5), from which 4-carbamoylphenyl 2-(4-isobutylphenyl)propanoate (3) was obtained (2.48 g, 40% yield).

Synthesis of 4-thiocarbamoylphenyl 2-(4-isobutylphenyl)propanoate(4)

4-carbamoylphenyl 2-(4-isobutylphenyl)propanoate, 3 (2.48 g, 7.62 mmol) and Lawesson reagent (3.1 g, 7.62 mmol) were dissolved in 130 ml of anhydrous benzene. The reaction was warmed to 60° C. and stirred for 4 h. The solvent was removed under reduced pressure. The obtained compound was purified by a silica gel open column and eluted with CH$_2$Cl$_2$/MeOH (9.5/0.5) giving the pure compound 4 (1.45 g, 55% yield).

$^1$H NMR (DMSO-d$_6$): δ 0.84 (d, 6H), 1.48 (d, 3H), 1.79-1.82 (m, 1H), 2.42 (d, 2H), 4.05 (dd, 1H), 7.05 (d, 2H), 7.15 (d, 2H), 7.28 (d, 2H) 7.88 (d, 2H), 9.49 and 9.87 (s, 2H, NH$_2$).

$^{13}$C NMR (DMSO-d$_6$): δ 19.2, 22.9, 30.3, 44.9, 121.6, 127.9, 129.5, 130.0, 137.8, 138.0, 140.8, 153.3, 173.3, 199.6.

MS (EI), m/e 341 (M$^+$);
m.p: 121-123° C.

Example 7

Synthesis of 4-thiocarbamoylphenyl 2-(4-oxophenyl)-phenyl propanoate

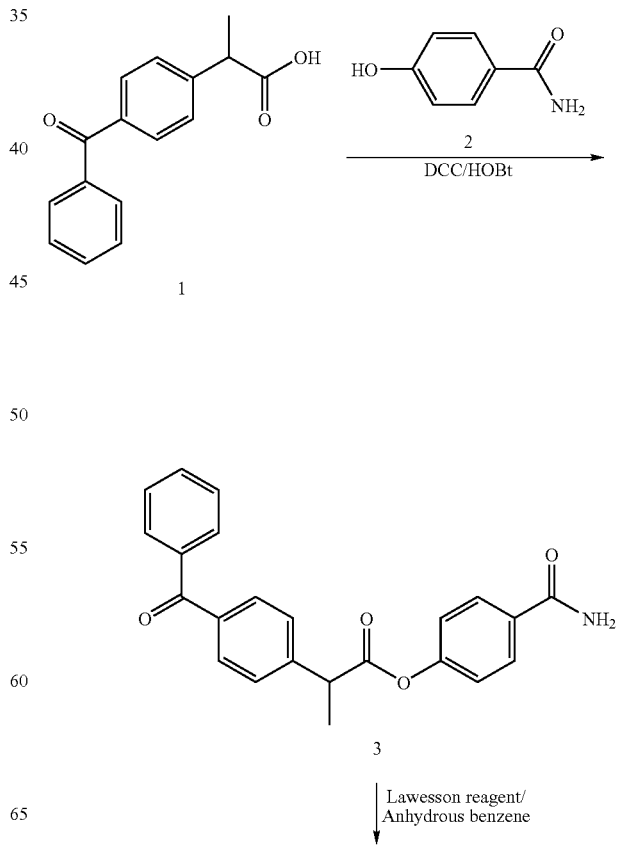

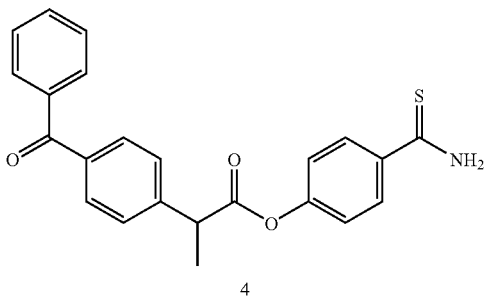

4

Synthesis of 4-carbamoylphenyl 2-(4-oxophenyl)-phenyl propanoate (3)

To the solution of 1 (ketoprofen, 3 g, 11.8 mmol) in 80 mL of dimethylformamide, hydroxybenzotriazole (1.76 g, 13 mmol) and DCC (2.68 g, 13 mmol) were added with stirring at 0° C. for 1 h. To the reaction mixture 4-hydroxybenzamide (2, 2.43 g, 17.7 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with $NaHCO_3$ 5%, with citric acid 10% and than dried on anhydrous $MgSO_4$, filtered and the solvent evaporated. The crude product 3 was loaded on a silica gel open column and eluted with $CH_2Cl_2$/MeOH (9.5/0.5), from which 4-carbamoylphenyl 2-(4-oxophenyl)-phenyl propanoate (3) was obtained (1.84 g, 42% yield).

Synthesis of 4-thiocarbamoylphenyl 2-(4-oxophenyl)-phenyl propanoate (4)

4-carbamoylphenyl 2-(4-oxophenyl)-phenyl propanoate (3) (1.84 g, 4.93 mmol) and Lawesson reagent (2 g, 4.93 mmol) were dissolved in 100 ml of anhydrous benzene. The reaction was warmed to 60° C. and stirred for 4 h. The solvent was removed under reduced pressure. The obtained compound was purified by a silica gel open column and eluted with $CH_2Cl_2$/MeOH (9.5/0.5) giving the pure compound 4 (0.45 g, 23% yield).

$^1$H NMR (DMSO-$d_6$): δ 1.53 (d, 3H), 4.25 (dd, 1H), 7.08 (d, 2H), 7.54-7.73 (m, 9H), 7.90 (d, 2H), 9.51 and 9.88 (s, 2H, $NH_2$).

$^{13}$C NMR (DMSO-$d_6$): δ 19.2, 44.9, 121.6, 129.3, 129.5, 129.8, 130.3, 132.6, 133.5, 137.6, 137.9, 138.1, 141.2, 153.3, 154.5, 156.1, 163.8, 172.9, 199.6.

MS (EI), m/e 390 (M$^+$);

m.p: 114-116° C.

Example 8

Synthesis of 4-thiocarbamoylphenyl 2-(3-fluoro, 4-phenyl)phenyl propanoate

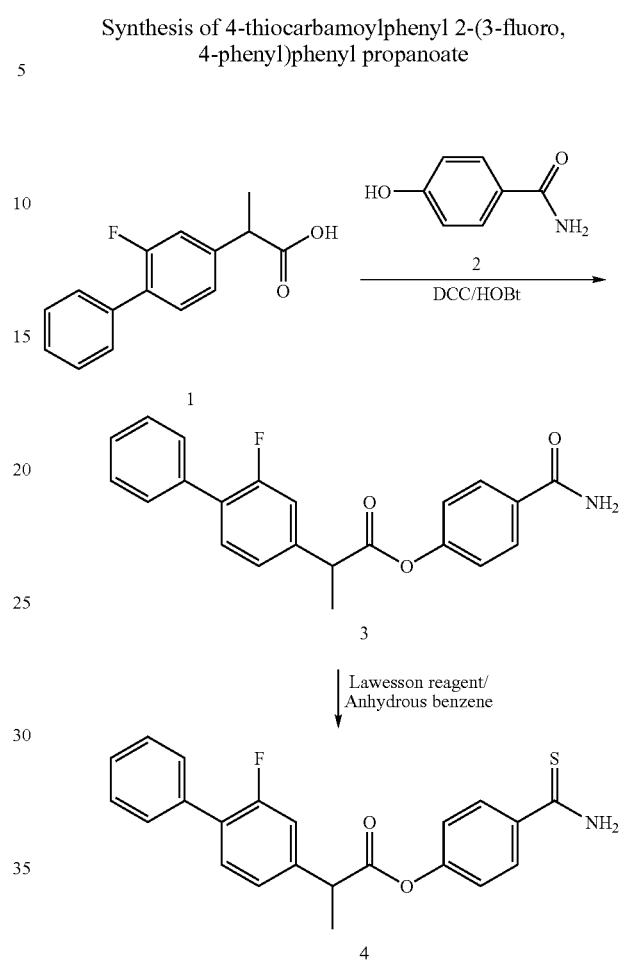

Synthesis of 4-carbamoylphenyl 2-(3-fluoro, 4-phenyl)phenyl propanoate (3)

To the solution of 1 (flurbiprofen, 2 g, 8.2 mmol) in 80 mL of dimethylformamide, hydroxybenzotriazole (1.22 g, 9.02 mmol) and DCC (1.86 g, 9.02 mmol) were added with stirring at 0° C. for 1 h. To the reaction mixture 4-hydroxybenzamide (2, 1.7 g, 12.2 mmol) was added and stirred for 1 h at 0° C. and 2 h at room temperature. After filtration, the filtrate was evaporated under reduced pressure to remove the solvent. The oily residue thus obtained was dissolved in ethyl acetate; the organic layer was washed with brine, with $NaHCO_3$ 5%, with citric acid 10% and than dried on anhydrous $MgSO_4$, filtered and the solvent evaporated. The crude product 3 was loaded on a silica gel open column and eluted with $CH_2Cl_2$/MeOH (9.5/0.5), from which 4-carbamoylphenyl 2-(3-fluoro, 4-phenyl)phenyl propanoate (3) was obtained (1.09 g, 37% yield).

Synthesis of 4-thiocarbamoylphenyl 2-(3-fluoro, 4-phenyl)phenyl propanoate (4)

4-carbamoylphenyl 2-(3-fluoro, 4-phenyl)phenyl propanoate, 3 (1.09 g, 3 mmol) and Lawesson reagent (1.21 g, 3 mmol) were dissolved in 70 ml of anhydrous benzene. The reaction was warmed to 60° C. and stirred for 4 h. The solvent was removed under reduced pressure. The obtained compound was purified by a silica gel open column and eluted with $CH_2Cl_2$/MeOH (9.5/0.5) giving the pure compound 4 (0.35 g, 31% yield).

$^1$H NMR (DMSO-$d_6$): δ 1.55 (d, 3H), 4.21 (dd, 1H), 7.32-7.55 (m, 8H), 7.90 (d, 2H), 9.51 and 9.88 (s, 2H, $NH_2$).

$^{13}$C NMR (DMSO-$d_6$): δ 19.1, 44.7, 115.9, 116.2, 121.7, 124.8, 128.6, 129.3, 129.4, 129.5, 131.7, 135.8, 137.7, 142.6, 153.7, 158.3, 163.5, 173.1, 199.6.

MS (EI), m/e 380 ($M^+$);

m.p: 142-144° C.

Example 9

General synthetic procedure of 4- or 5-Amino-2-hydroxy-benzoic acid 4-thiocarbamoyl-phenyl ester (8) (also referred to as Compound XXVII)

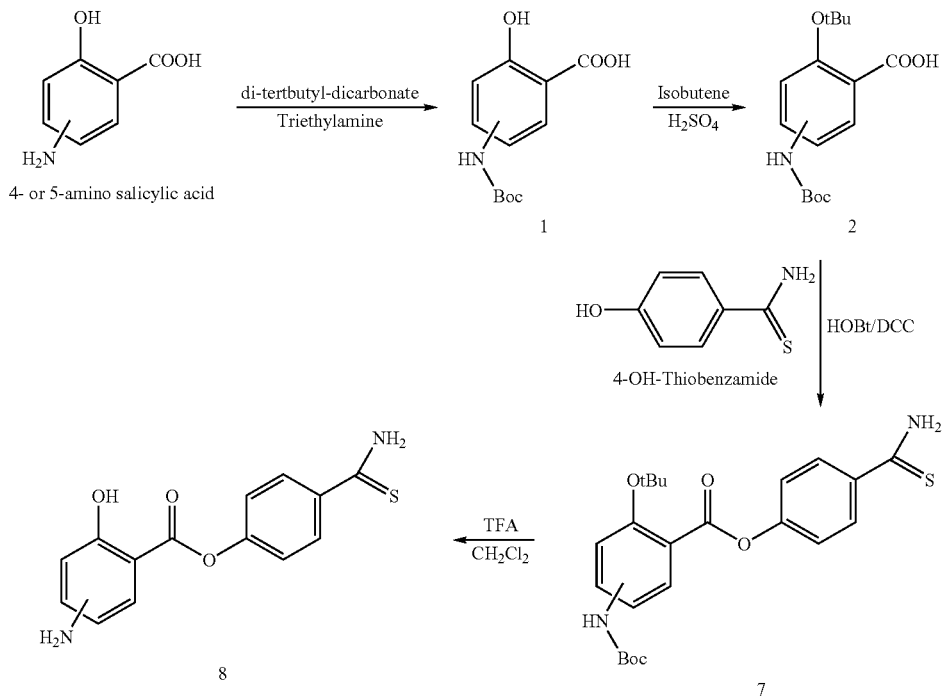

Synthesis of 4- or 5-tert-Butoxycarbonylamino-2-hydroxy-benzoic acid (1)

To the solution of 4- or 5-amino salicylic acid (10.0 mmol) in 25 mL of dioxane and 12.5 mL of water, triethylamine (15.0 mmol) and di-tert-butyl-dicarbonate (15.0 mmol) were added with stirring at 0° C. for ½ h. The reaction mixture was stirred mechanically for 24 h at room temperature. After evaporation of the solvent, 3M HCl (15 mL) was added drop wise to the residue. The precipitate is filtered, washed with water and dried. The residue was loaded on a silica gel open column and eluted with $CH_2Cl_2$/MeOH (9/1), from which 4- or 5-tert-Butoxycarbonylamino-2-hydroxy-benzoic acid (1) was obtained (80% yield).

Synthesis of 4- or 5-tert-Butoxycarbonylamino-2-tert-butoxy-benzoic acid (2)

Compound (1) (12.0 mmol), conc. $H_2SO_4$ (6.0 mmol), and DCM (100 mL) were stirred under isobutylene gas (5 psi) for 6 h at rt. The solution was washed with cold 10% $NaHCO_3$ (2×100 mL) and brine (100 mL), dried ($Na_2SO_4$) and evaporated. The residue was dissolved in 1:1 MeOH/$CCl_4$ (400 mL), washed with water (300 mL), and then extracted with 1:1 MeOH/water (2×200 mL). The extract was dried ($Na_2SO_4$) and evaporated to a white solid (2), which was recrystallized by DCM/hexane (83% yield).

Synthesis of 4- or 5-Amino-2-hydroxy-benzoic acid 4-thiocarbamoyl-phenyl ester (8)

To the solution of 4- or 5-tert-butoxycarbonylamino-2-hydroxy-benzoic acid (2) (3.0 mmol) in 50 mL of dimethyl-formamide, hydroxybenzotriazole (3.3 mmol) and DCC (3.3 mmol) were added with stirring at 0° C. for 1 h. To the reaction mixture, 4-hydroxy-thiobenzamide (3.0 mmol) was added and stirred mechanically for 3 h at 0° C. and 72 h at room temperature. After filtration, the filtrate was evaporated under reduced pressure to remove the solvent. The oily residue thus obtained was dissolved in ethyl acetate; the organic layer was washed with brine, dried on anhydrous $MgSO_4$, filtered and the solvent evaporated. The crude intermediate (7) was treated with a solution of 40% TFA in $CH_2Cl_2$. After 2 h the solvent was removed to obtain compound (8) as a crude residue. The residue was loaded on a silica gel open column and eluted with $CH_2Cl_2$/MeOH (8/2), from which 4- or 5-Amino-2-hydroxy-benzoic acid 4-thiocarbamoyl-phenyl ester (8), compound of Formula XXVII, was obtained (48% yield).

Example 10

Synthesis of Trimebutine Thiocarbamoylbenzoate

Preparation of 3,4,5-trimethoxybenzoic acid 2-(dimethylamino)-2-phenylbutyl ester 4-thiocarbamoyl benzoate (Trimebutine thiocarbamoylbenzoate)

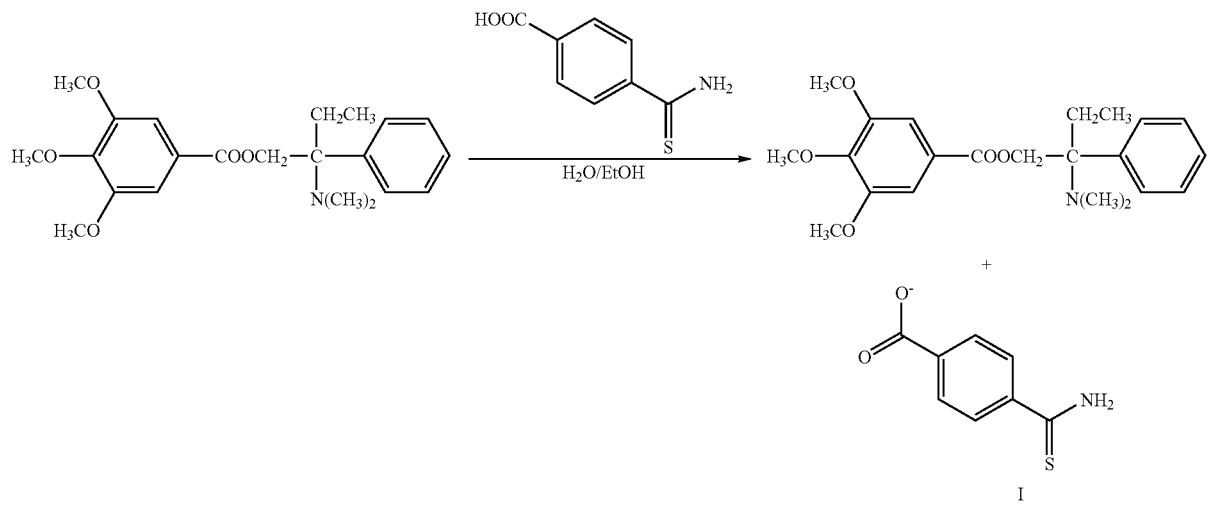

To a mixture of 4-(thiocarbamoyl)benzoic acid (0.1 mol) and trimebutine (0.1 mol), water (200 mL) and ethyl alcohol (20 mL) have been added and the resulting suspension has been stirred at room temperature until clear. Then the solution has been frozen and lyophilized furnishing the desired salt (quantitative yield).

$^1$H-NMR (400 MHz, DMSO-$d_6$): δ 0.60 (t, 3H), 1.45-1.75 (m, 4H), 1.80-1.90 (m, 2H), 2.28 (s, 6H), 2.90-3.40 (m, 2H), 3.69 (s, 9H), 3.95 (m, 1H), 4.73 (dd, 2H), 7.01 (s, 2H), 7.22 (t, 1H), 7.35 (t, 2H), 7.46 (d, 2H) 7.93 (dd, 4H), 9.65 (bs, 1H, NH), 10.05 (bs, 1H, NH).

$^{13}$C-NMR (400 MHz, DMSO-$d_6$): δ 9.07, 28.9, 56.5, 60.8, 64.5, 65.7, 107.1, 125.3, 127.4, 128.1, 128.6, 129.5, 129.7, 132.3, 141.8, 142.5, 148.5, 153.4, 154.8, 165.9, 169.4, 172.5, 188.6.

mp 66-68° C. (dec).

Synthesis of 4-(thiocarbamoyl)benzoic acid

The compound was synthesized according to a procedure already reported in literature (Fairfull, E. S., Lowe J. L., Peak D. A. *J. Chem. Soc.* 1952, 742), incorporated herein by reference.

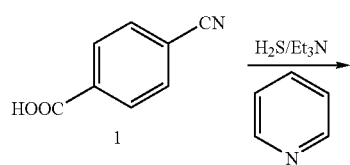

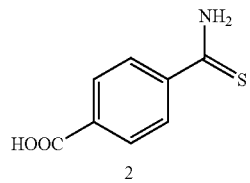

4-(Thiocarbamoyl)benzoic acid (2)

3 g of 4-cyanobenzoic acid 1 (20.4 mmol) were dissolved in 40 mL of pyridine and 2.1 mL of triethylamine (20.4 mmol) were added. Dry hydrogen sulphide was passed through the solution in a steady steam for 4 h. The mixture was then poured into water and the solid collected by filtration. Recrystallization from petroleum ether furnished 2.51 g of the pure compound 2 (68% yield).

MS (ESI), m/e 182.2 (M$^+$).

$^1$H NMR (DMSO-$d_6$): δ 7.92 (dd, 4H), 9.68 (s, 1H, NH), 10.12 (s, 1H, NH), 13.25 (s, 1H, OH).

$^{13}$C NMR (DMSO-$d_6$): δ 127.3, 129.6, 132.0, 148.5, 169.4, 188.6 m.p. 296-298° C. (dec.)

Example 11

Synthesis of Succinic acid 2-{2-[8-(2,2-dimethyl-butyryloxy)-2,6-dimethyl-1,2,6,7,8,8a-hexahydro-naphthalen-1-yl]-ethyl}-6-oxo-tetrahydro-pyran-4-yl ester 4-thiocarbamoyl-phenyl ester (3) (also referred to as Compound I)

Synthesis of Succinic acid 4-carbamoyl-phenyl ester 2-{2-[8-(2,2-dimethyl butyryloxy)-2,6-dimethyl-1,2,6,7,8,8a-hexahydro-naphthalen-1-yl]-ethyl}-6-oxo-tetrahydro-pyran-4-yl ester (2)

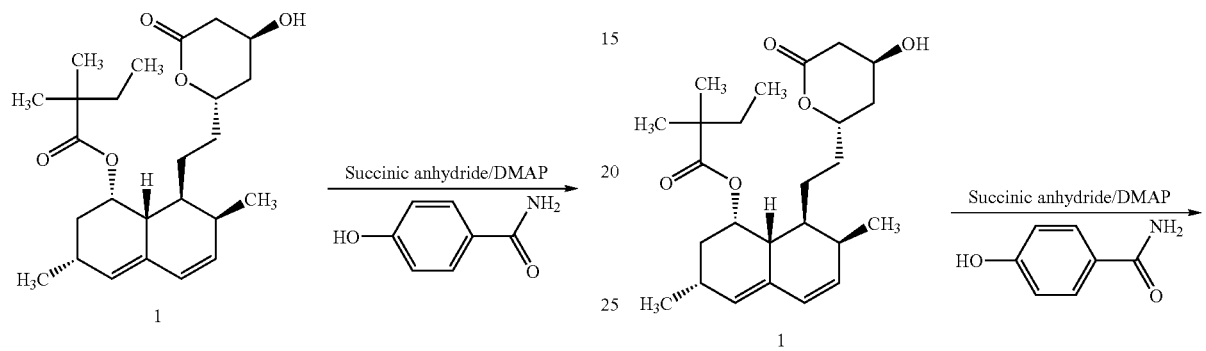

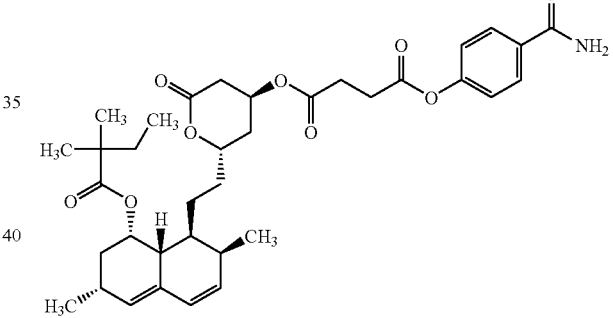

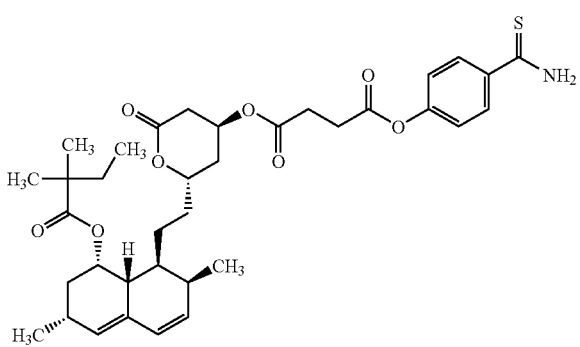

A solution of 420 mg (0.001 mole) of simvastatin (1) in 3 ml of dichloromethane was treated with 110 mg of succinic anhydride and 10 mg of DMAP. After 36 h, 210 mg (0.001 mole) of EDCI and 170 mg (0.0012 mole) of 4-hydroxy-benzamide was added under stirring.

After 1 h, the solvent was removed under reduced pressure and the crude residue was purificated by silica gel column eluting with dichloromethane/methyl alcohol (9.5/0.5) to yield compound 2 as a white solid (350 mg; 55% yield).

MS (EI), m/e 638 (M$^+$);

$^1$H NMR (DMSO) δ 0.831 (m, 6H, 2-Me), 1.075 (m, 9H, 3-Me), 1.53 (m, 6H), 1.97 (m, 2H), 2.27 (m, 5H), 2.52 (d, 2H), 2.62 (d, 2H), 3.68 (m, 1H), 4.07 (m, 1H), 5.52 (m, 1H), 5.50 (bt, 1H), 5.77 (dd, 1H), 5.96 (d, 1H); 7.08 (d, 2H), 7.87 (d, 2H), 7.94 (bs, 2H).

Synthesis of succinic acid 2-{2-[8-(2,2-dimethyl-butyryloxy)-2,6-dimethyl-1,2,6,7,8,8a-hexahydro-naphthalen-1-yl]-ethyl}-6-oxo-tetrahydro-pyran-4-yl ester 4-thiocarbamoyl-phenyl ester (3)

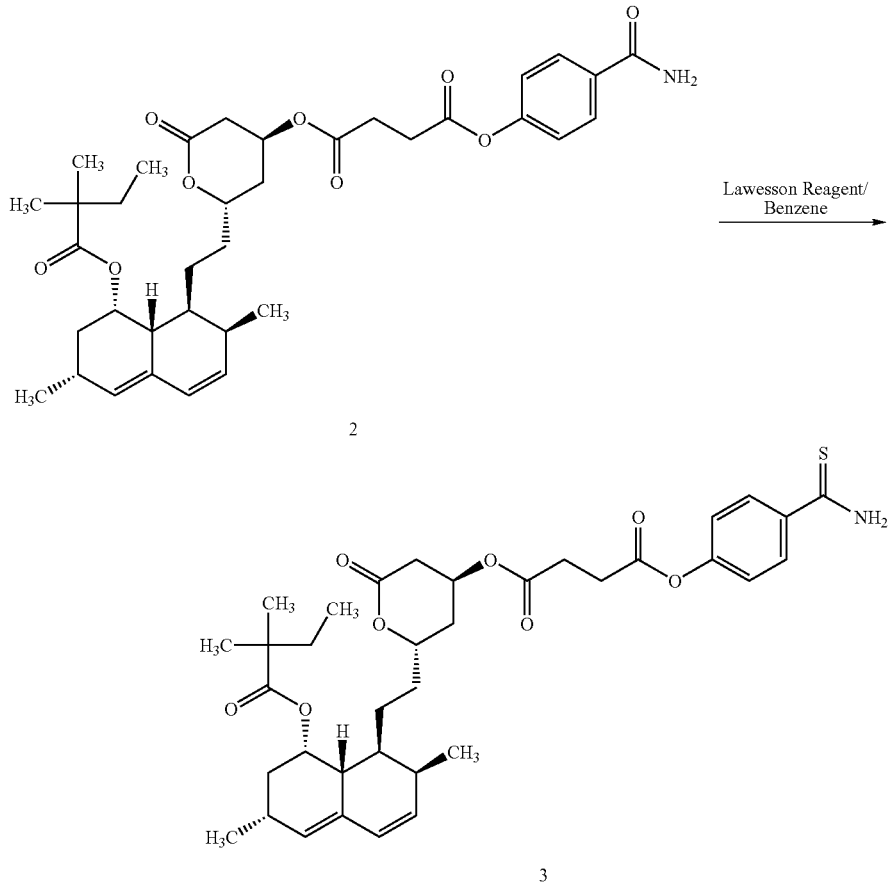

Succinic acid 4-carbamoyl-phenyl ester 2-{2-[8-(2,2-dimethyl-butyryloxy)-2,6-dimethyl-1,2,6,7,8,8a-hexahydro-naphthalen-1-yl]-ethyl}-6-oxo-tetrahydro-pyran-4-yl ester (2) (0.35 g, 0.000548 mol) and Lawesson reagent (0.221 g, 0.000548 mol) were dissolved in 30 ml of anhydrous benzene. The reaction was warmed to 50° C. and stirred for 6 h. The solvent was removed under reduced pressure; the crude residue was purificated by silica gel column (dichloromethane/methyl alcohol 9.5:0.5) to furnish 35 mg of the pure compound 3 (10% yield).

MS (EI), m/e 654 (M$^+$);
$^1$H NMR (DMSO) δ 0.831 (m, 6H, 2-Me), 1.075 (m, 9H, 3-Me), 1.53 (m, 6H), 1.97 (m, 2H), 2.27 (m, 5H), 2.52 (d, 2H), 2.62 (d, 2H), 3.68 (m, 1H), 4.07 (m, 1H), 5.52 (m, 1H), 5.50 (bt, 1H), 5.77 (dd, 1H), 5.96 (d, 1H); 7.11 (d, 2H), 7.9 (d, 2H), 9.48 (s, 1H), 9.86 (s, 1H).

Testing of Compounds

Example 12

Comparison of Disease Activity Index and MPO Activity of 5-Amino-2-(4-thiocarbamoyl-phenoxy-carbonyloxy)-benzoic acid A standard experimental animal model of colitis induced by intracolonic administration of 2,4,6-trinitrobenzene sulfonic acid (TNBS) to mice is used in the following example. A detailed description of this model has been published (Santucci et al. (2003) Gastroenterology 124:1381-94) and is incorporated herein by reference. Briefly, 6-8 week old Balb/c mice were given TNBS intracolonically at a dose of 1.5 mg in 0.1 mL of 30% ethanol. The mice were randomized to the various treatment groups (n=6 per group). Beginning one hour later and continuing every 12 h for 5 days, the mice were treated orally with vehicle (1% carboxymethylcellulose (CMC)), 5-ASA (mesalamine) alone (100 mg/kg), 4-hydroxythiobenzamide (referred to in the Figures as 4-HTB) (100 mg/kg), 5-amino-2-(4-thiocarbamoyl-phenoxycarbonyloxy)-benzoic acid (100 mg/kg) (referred to hereinafter as Compound XXVII) and equimolar doses of mesalamine (50 mg/kg) and (4-HTB) (50 mg/kg). *p<0.05 versus the vehicle-treated group. Each group consisted of at least 5 rats.

The mice were evaluated (blindly) on the final day of the study for the presence of diarrhea and fecal occult blood, and their body weights were measured. A "disease activity score" was calculated based on these data (0 to 4 scale, as outlined in the paper cited above). After sacrifice, a sample of the colon was excised for measurement of myeloperoxidase (MPO) activity, as a marker of granulocyte infiltration. All results were compared to those obtained with healthy mice as well.

Figure 2:
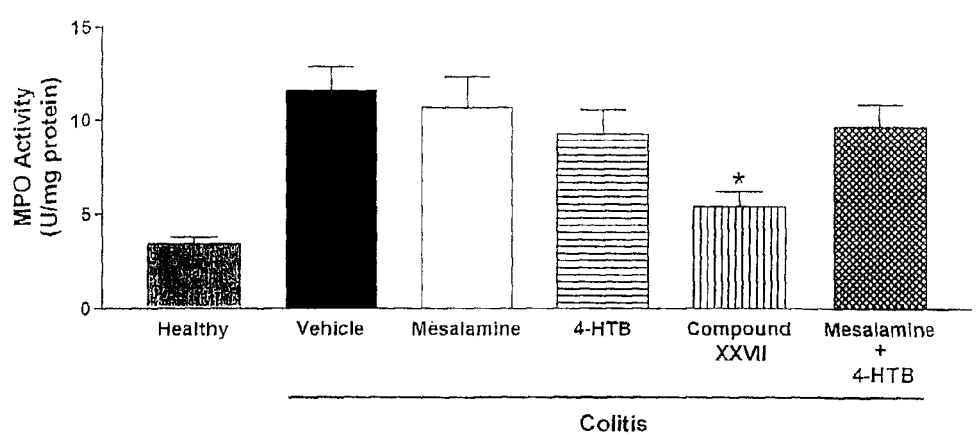
FIG. 2 shows the myeloperoxidase (MPO) activity in mice having TNBS-induced colitis after treatment with 5-amino-2-(4-thiocarbamoyl-phenoxycarbonyloxy)-benzoic acid (Compound XXVII), mesalamine alone, 4-HTB alone and a mixture of mesalamine and 4-hydroxythiobenzamide (4-HTB).

FIG. 1 shows that Compound XXVII is almost three times as effective as either mesalamine alone, 4-HTB alone or a mixture of mesalamine and 4-HTB in reducing disease symptoms. Further, FIG. 2 shows that Compound XXVII significantly reduced inflammation as indicated by the reduction in granulocyte infiltration (reduced MPO activity).

Example 13

Comparison of the Effects of 5-Amino-2-(4-thiocarbamoyl-phenoxycarbonyloxy)-benzoic acid versus Mesalamine in a Rat Model of Visceral Pain Perception A rat model of visceral pain perception, a pre-clinical model of irritable bowel syndrome, was used in the following example. Rats (male, Wistar, 200-250 g, obtained from Charles River, Monza, Italy), were housed in plastic cages and maintained under controlled conditions with 12-hours light/dark cycle with lights on at 7.00 AM. Tap water and standard laboratory chow were freely available. Before experiments, rats were individually trained by spending 2-3 hours per day in a plexiglass cage for 2-3 days. It allowed them to adjust to a movement-restriction environment. Food was withheld for 12 hours before colorectal distension (CRD) recording were performed. Experiments were performed in awake rats and were conducted in a blind manner in that the observer was not aware of the identity of drug administered to each animal.

In the testing day, rats were sedated with ether inhalation and a 2 cm long latex balloon was inserted intrarectally 2 cm from the anal verge and fixed at the base of the tail. The balloon was connected via a double-barreled cannula to a pressure transducer to continuously monitoring the rectal pressure by a computer (PowerLab PC, A.D. Instruments, Milford, Mass., USA) and to a syringe for inflation/deflation of the balloon. The rats were then housed in a small cage (20×8×8 cm) on an elevated Plexiglas™ platform and allowed to wake up and adapt for 1 hour. After recovery from sedation, animals underwent the CRD procedure and behavioral responses were tested. The night before the experiments, the balloons were inflated and left overnight so the latex stretched and the balloons became compliant.

CRD of 20 seconds, performed every 5 minutes, was applied in increment of 0.4 ml starting from 0.4 ml up to 1.6 ml water. To achieve an accurate measurement of the colonic parameters and perception, the distensions were repeated twice for each intensity and data for each animal were averaged for analysis. Each animal underwent a double set of CRD. Twenty minutes after the first sequence of CRD (0.4 mL-1.6 ml water), drugs were administered intraperitoneally (i.p.) and a second set of CRD was performed. Behavioral responses during the first and the second set of CRD were assessed and compared.

Behavioral response to CRD was assessed by measuring the abdominal withdrawal reflex (AWR) using a semiquantitative score (1). The AWR is an involuntary motor reflex similar to the visceromotor reflex, but it has the great advantage that, in contrast to the latter, it does not require abdominal surgery to implant recording electrodes and wires in the abdominal muscle wall which may cause additional sensitization (see Ness, T. J. and Gebhart, G. F. (1990) *Pain* 41:167-234, incorporated herein by reference).

Measurement of the AWR consisted of visual observation of the animal response to graded CRD by blinded observer and assignment of an AWR score according with the behavioral scale as previously described in Al-Chaer, E. D. et al. (2000) *Gastroenterology* 19: 1276-85, incorporated herein by reference, in which grade 0 corresponds to no behavioral response to CRD, grade 1 corresponds to brief head movement at the onset of the stimulus followed by immobility, grade 2 corresponds to a mild contraction of abdominal muscles although the rats does not lift the abdomen off the platform, grade 3 corresponds to a strong contraction of the abdominal muscles with the lifting of the abdomen off the platform, and grade 4 corresponds to a severe contraction of the abdominal muscle manifested by body arching and the lifting of the abdomen and of the pelvic structures and scrotum.

A rat model of visceral pain perception as described above was used to compare pain perception scores for 5-amino-2-(4-thiocarbamoyl-phenoxycarbonyloxy)-benzoic acid (Compound XXVII) with or without glibenclamide, an inhibitor of ATP-sensitive $K^+$ ($K_{ATP}$) channels.

Figure 3:
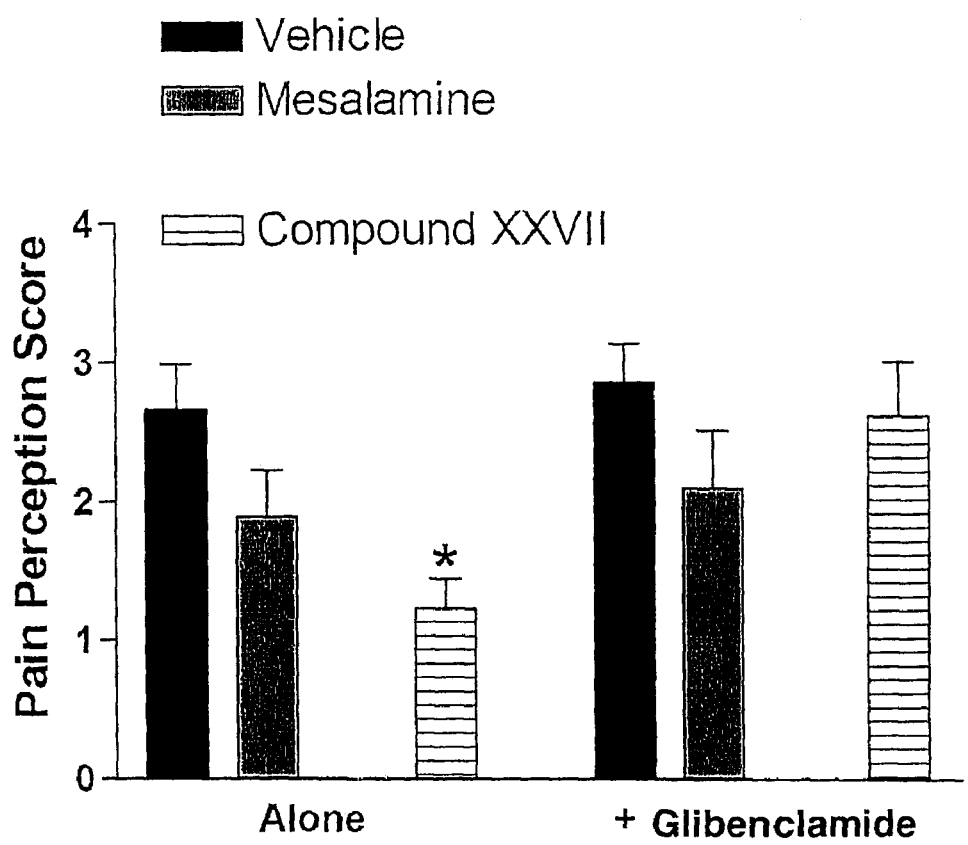
FIG. 3 shows the pain perception scores of mesalamine and 5-amino-2-(4-thiocarbamoyl-phenoxycarbonyloxy)-benzoic acid (Compound XXVII) with or without glibenclamide.
Figure 4:
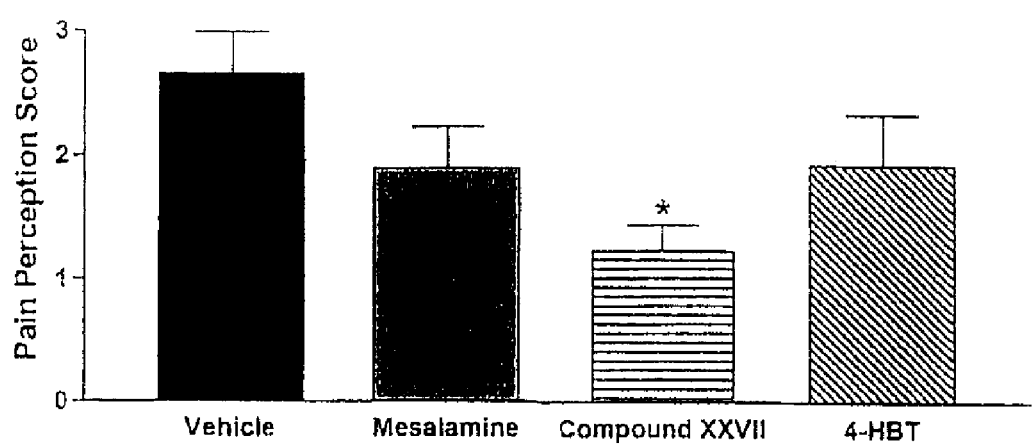
FIG. 4 shows the pain perception scores of 5-amino-2-(4-thiocarbamoyl-phenoxycarbonyloxy)-benzoic acid (Compound XXVII), mesalamine and 4-hydroxythiobenzamide (4-HBT).

FIG. 3 shows the pain perception score in response to 0.8 mL of colorectal distention in groups of rats (at least 5 per group) treated with vehicle, mesalamine (100 mg/kg), and Compound XXVII (100 mg/kg). Compound XXVII significantly reduced the pain perception (*$p<0.05$ versus the vehicle-treated group), while mesalamine had no significant effect. The reduction of pain perception by Compound XXVII was reversed by pretreatment with glibenclamide (10 mg/kg i.p. 30 min before), while glibenclamide pretreatment did not affect the pain perception in the groups treated with vehicle or mesalamine, suggesting that the anti-nociceptive activity of Compound XXVII may be mediated by ATP-sensitive $K^+$ ($K_{ATP}$) channels. FIG. 4 shows that 4-hydroxythiobenzamide (4-HTB) alone (100 mg/kg) did not have a significant effect on pain perception.

Example 14

Effect of 5-Amino-2-(4-thiocarbamoyl-phenoxycarbonyloxy)-benzoic acid on Leukocyte Adherence to the Vascular Endothelium In Vivo Leukocyte adherence was studied using intravital microscopy, as described in detail previously (Wallace et al., (1993) *Am. J. Physiol.* 265: 993-998, incorporated hereto by reference). Rats were anesthetized with pentobarbital sodium (60 mg/kg i.p.) and cautery incisions were made along the abdominal region. A tracheotomy was performed to facilitate breathing. The rats were placed in a supine position, and a segment of the mesentery was exteriorized through the abdominal incision. The mesentery was carefully placed over an optically clear viewing pedestal that allowed for trans-illumination of a 2-$cm^2$ segment of tissue. All exposed tissue was covered with saline-soaked gauze to minimize dehydration. The temperature of the pedestal was kept at 37° C. and the mesentery was superfused with warmed bicarbonate-buffered saline (pH 7.4). An intravital microscope (Nikon L25/0.35) and a ×10 eyepiece were used to observe the mesenteric microcirculation. Post-capillary venules with diameters ranging from 20 to 40 μm were selected for the study. A video camera mounted on the microscope (Panasonic™ digital 5000) projected the image onto a monitor, and the images were recorded for playback analysis using a videocassette recorder. Images of the mesenteric microcirculation were recorded 5 minutes prior to aspirin administration (baseline), at the time of aspirin administration (time 0-5) and every 15 minutes for 60 minutes. Leukocyte adherence was blindly quantified from videotaped images of the vessels made over 5-min periods as the number of leukocytes that remained stationary along the vessel wall for 30 s or more (expressed per 100 μm venule length). Groups of rats (at least 5 in each) were pretreated with 5-Amino-2-(4-thiocarbamoyl-phenoxycarbonyloxy)-benzoic acid (Compound XXVII)

(100 mg/kg), mesalamine (50 mg/kg), or vehicle 60 min prior to aspirin (or vehicle) administration. These drugs were given intragastrically. In some experiments, rats were treated with glibenclamide (10 mg/kg i.p.) or vehicle 30 min prior to administration of these compounds.

Figure 5:
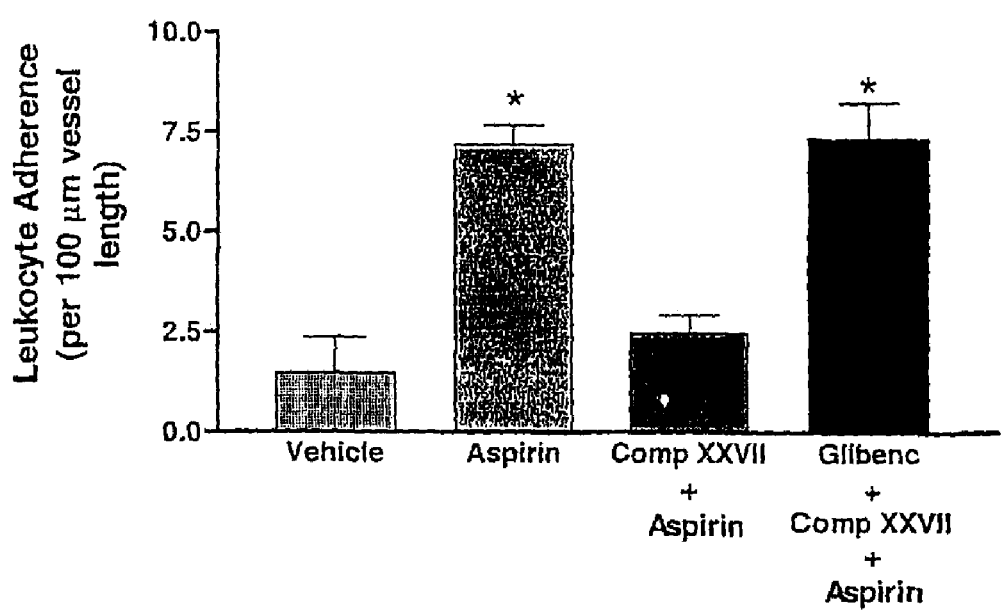
FIG. 5 is a bar graph of the leukocyte adherence at 60-65 minutes for 5-amino-2-(4-thiocarbamoyl-phenoxycarbonyloxy)-benzoic acid (Compound XXVII) in the presence of aspirin or aspirin plus glibenclamide.

FIG. 5 shows leukocyte adherence for the final time period of the experiment (minutes 60-65). This graph illustrates the ability of Compound XXVII to suppress aspirin-induced leukocyte adherence, and the ability of glibenclamide pretreatment to reverse this inhibitor effect on leukocyte adherence.

Example 15

Figure 6:
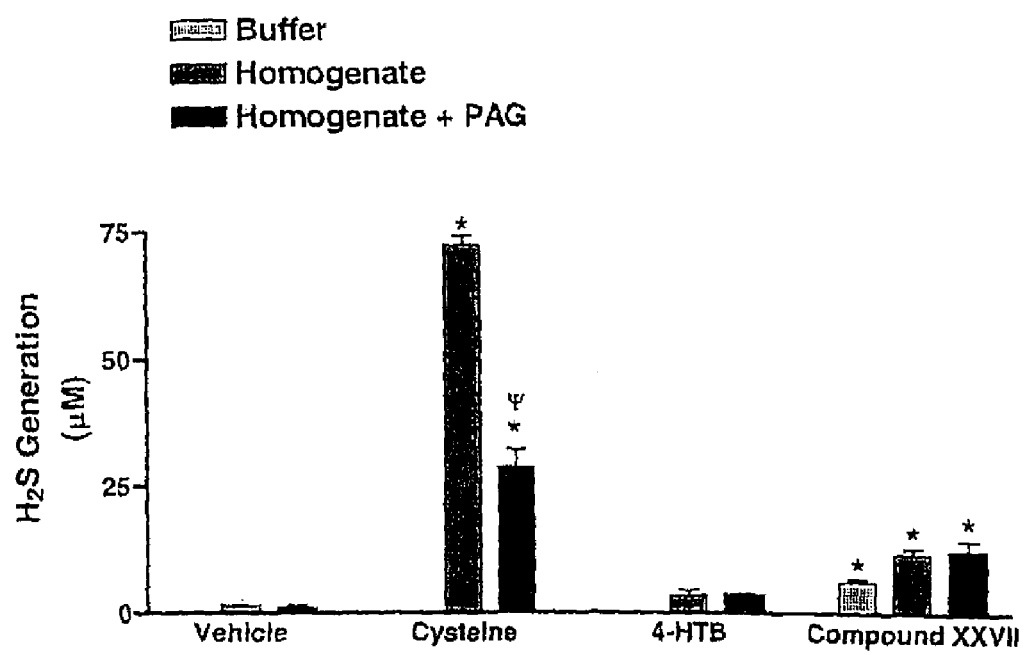
FIG. 6 is a bar graph showing $H_2S$ generation of cysteine, 5-amino-2-(4-thiocarbamoyl-phenoxycarbonyloxy)-benzoic acid (Compound XXVII) and 4-hydroxythiobenzamide (4-HBT).

Generation of $H_2S$ by 5-Amino-2-(4-thiocarbamoyphenoxycarbonyloxy)-benzoic acid 5-Amino-2-(4-thiocarbamoyl-phenoxycarbonyloxy)-benzoic acid (Compound XXVII) was tested for $H_2S$ generation under three different conditions. Concentrations of $H_2S$ that were generated within 1 hour from 1 mM concentrations of L-cysteine, 4-HBT (4-hydroxythiobenzamide) and 5-amino-2-(4-thiocarbamoyl-phenoxycarbonyloxy)-benzoic acid were measured. $H_2S$ release was tested under three conditions: (i) when the compound was in buffer, (ii) when the compound was in a liver homogenate, and (iii) when the compound was in the liver homogenate together with an inhibitor of cystathionine γ-lyase (PAG=DL-propargylglycine; 2 mM). Results are shown in FIG. 6. *p<0.05 compared to the release from the vehicle group. ᵠp>0.05 versus the corresponding 'homogenate' group. The enzymatic capacity for $H_2S$ production was determined using the same reactor as described previously (Khan et al. (1980) *Microchem J* 25: 388-395, incorporated herein by reference). Two ml of an assay reaction mixture was introduced in the reactor. The mixture contained 1 mM L-cysteine (or compound), 2 mM pyridoxal 5'-phosphate, 100 mM potassium phosphate buffer (pH=7.4). A constant stream of nitrogen was passed through the mixture via gas-inlet capillary. Reactions were initiated by transferring the tubes from ice bath to a 37° C. water bath. The stream of nitrogen carried the sulfide acid in the second reactor containing 4 ml of sulfide anti-oxidant buffer (SAOB) solution, consisting of 2M KOH, 1M salicylic acid and 0.22M ascorbic acid at pH 12.8[5]. After incubating at 37° C. for 90 minutes, 1 ml of 10% trichloroacetic acid solution was added to mixture to stop the reaction. The remainder $H_2S$ in the mixture was carried out via nitrogen stream by other 60 minutes of incubation at 37° C. The concentration of sulfide in SAOB solution was measured with a sulfide sensitive electrode (Model 9616 $S^{2-}/Ag^+$ electrode, Orion Research, Beverly, Mass., USA). For studies in which the test compounds were incubated in liver homogenate, 100-150 mg of isolated rat livers were homogenized in 1 ml of ice-cold T-PER protein extractor. The homogenates were added to the reaction mixture at a concentration of 10% (wt/vol). DL-propargylglycine 2 mM was incubated with liver homogenates for 5 min at 37° C. prior the enzyme reaction. Khan, S. U. Morris, G. F. and Hidiroglou, M. (1980) Rapid estimation of sulfide in rumen and blood with a sulfide-specific ion electrode. *Microchem J.* 25:388-395, incorporated herein by reference.

The results shown in FIG. 6 suggest that Compound XXVII has the following distinct features:

1. Compound XXVII releases $H_2S$ spontaneously (in buffer), which is desirable for a topical effect in the gut. 4-HTB and L-cysteine did not release significant $H_2S$ when incubated only in buffer;
2. The release of $H_2S$ is greater when in the presence of tissue;
3. The release of $H_2S$ from Compound XXVII occurs independent of the activity of the two main enzymes for endogenous synthesis of $H_2S$ (cystathionine β-synthase and cystathionine-γ-lyase). This is demonstrated by lack of effect of an inhibitor of those enzymes (PAG; DL-propargylglycine), on $H_2S$ generation from Compound XXVII. In contrast, the release of $H_2S$ from L-cysteine is markedly inhibited by PAG;
4. The concentration of $H_2S$ produced from Compound XXVII is in the 10-20 uM range when 1 mM of the compound was used. Concentrations of up to 5 mM mesalamine can be measured in the colonic lumen after patients have taken the usual doses of this drug (*Dig. Dis. Sci.* 1989; 34: 573-578). Endogenous concentrations of $H_2S$ can be as much as 160 μM (*Antioxid. Redox Signal.* 2003; 5, 493-501). Compound XXVII releases $H_2S$ at concentrations within the physiological range thereby minimizing the chances of $H_2S$-related toxicity.

Example 16

Comparison of the Effects of Trimebutine Thiocarbamoylbenzoate versus Trimebutine Alone and Thiocarbamoylbenzoate Alone, in a Rat Model of Visceral Pain Perception Experiments were carried out as described in Example 13, except that groups of 5 rats each were treated with vehicle, trimebutine maleate (10 mg/kg), or with equimolar doses of trimebutine thiocarbamoylbenzoate (Compound III) or thiocarbamolybenzoate alone.

Figure 7A:
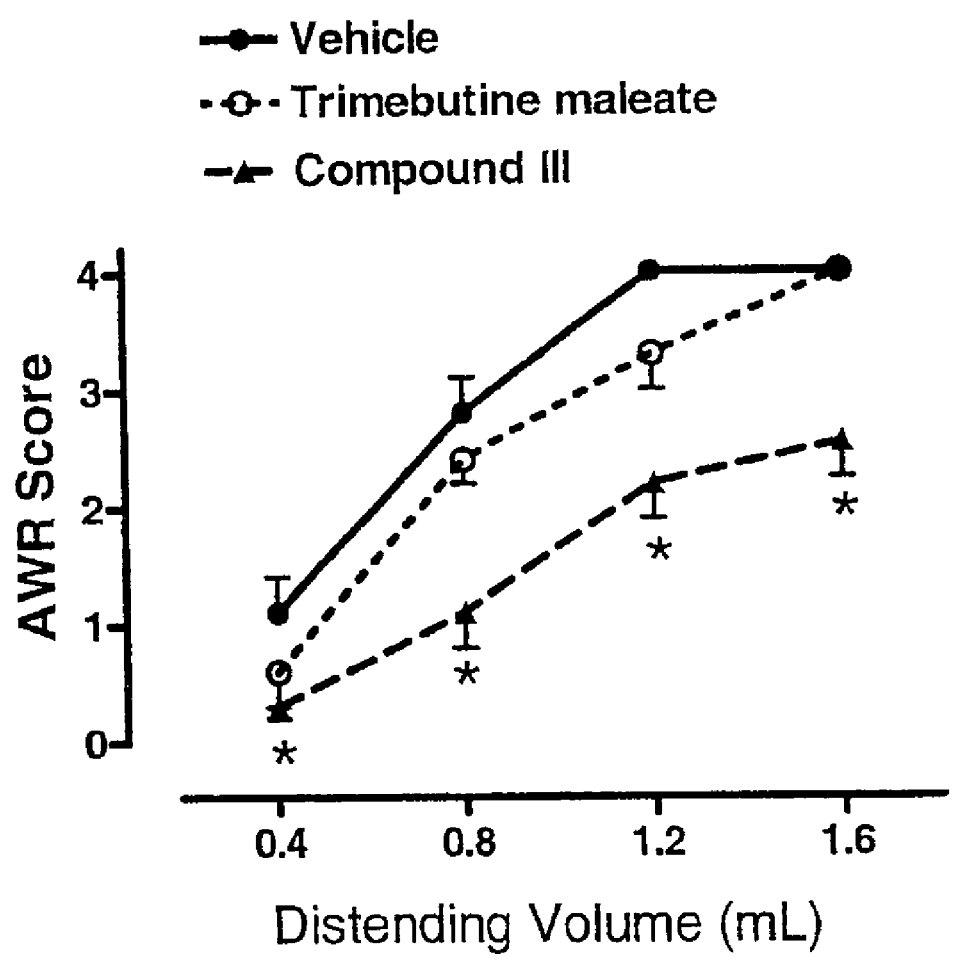
FIG. 7a shows the perception score (AWR Score) in a rat model of visceral pain perception using vehicle, trimebutine maleate and trimebutine thiocarbamoylbenzoate (Compound III).
Figure 7B:
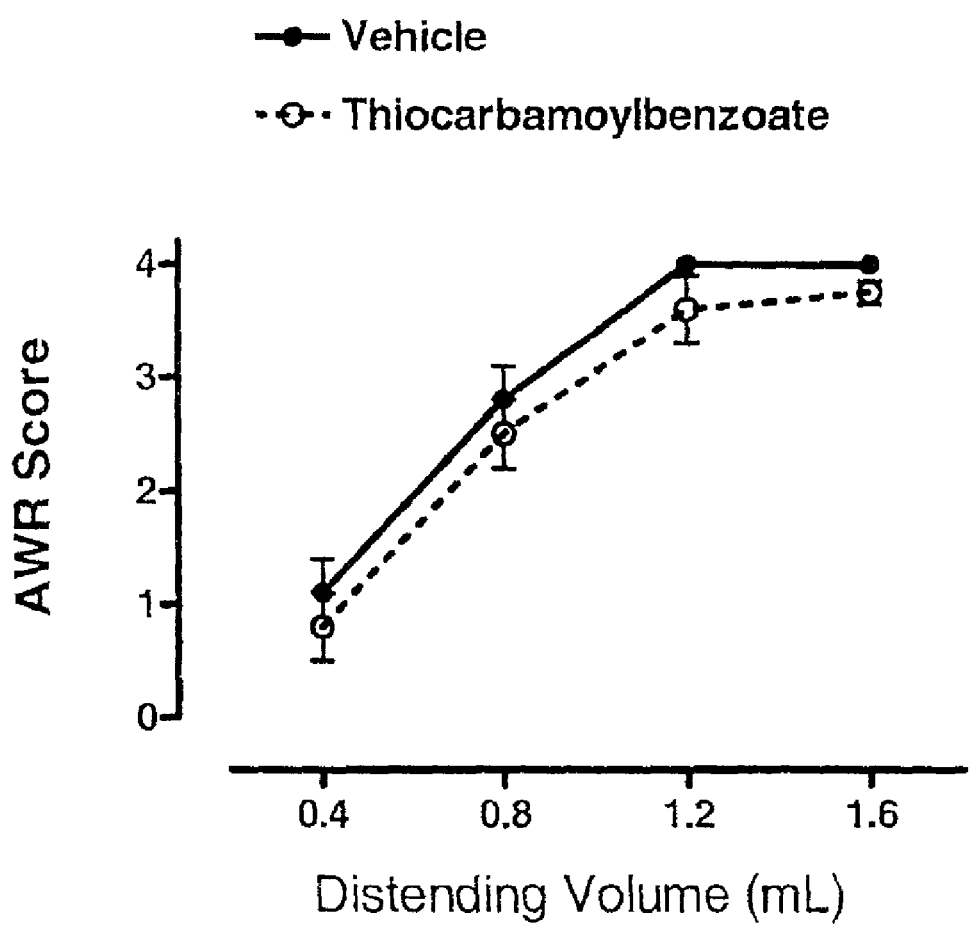
FIG. 7b shows the perception score (AWR Score) in a rat model of visceral pain perception using vehicle and thiocarbamoylbenzoate alone.

FIGS. 7(*a*) and 7(*b*) show that trimebutine thiocarbamoylbenzoate is more effective than either trimebutine maleate or thiocarbamoylbenzoate in reducing visceral pain in response to colorectal distension.

Thus, trimebutine thiocarbamoylbenzoate is useful in treating abdominal pain associated with various inflammatory conditions of the alimentary tract, as well as functional gastrointestinal disorders such as irritable bowel syndrome, dyspepsia, etc., that are characterized by increased visceral nociception (with or without accompanying inflammation).

Example 17

Gastrointestinal Safety of the NSAID Compounds of the Present Invention

The diclofenac derivative, [2-(2,6-dichloro-phenylamino)-phenyl]-acetic acid 4-thiocarbamoyl-phenyl ester, of the present invention, also referred to herein as Compound XVII, was evaluated for its gastrointestinal safety in rats. In particular, gastric damage, gastric $PGE_2$ synthesis, small intestine ulceration and hematocrit were measured.

Male Wistar rats weighing 175-200 g were fasted for 18 h prior to oral administration of 1% carboxymethylcellulose (vehicle; 0.2 mL) alone, or one of the following dissolved in this vehicle: diclofenac (20 mg/kg), [2-(2,6-dichloro-phenylamino)-phenyl]-acetic acid 4-thiocarbamoyl-phenyl ester (Compound XVII) (27.3 mg/kg), 4-hydroxythiobenzamide (TBZ) (7.3 mg/kg) or diclofenac plus TBZ. The dose of Compound XVII is equimolar to a 20 mg/kg dose of diclofenac. Similarly, the dose of TBZ is equimolar to the dose of Compound XVII.

Figure 8:
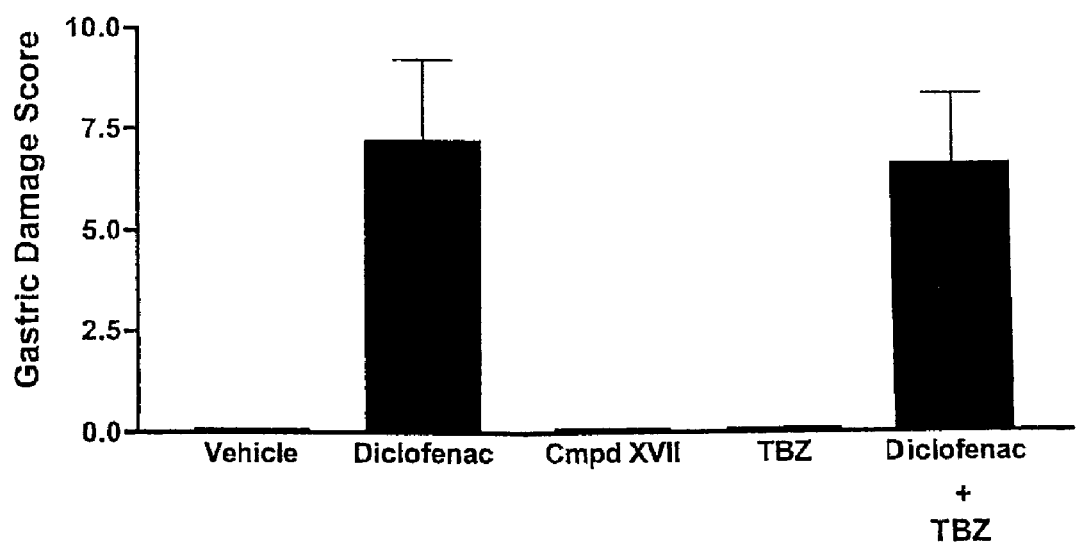
FIG. 8 illustrates the gastric damage score measured in rats treated with vehicle, diclofenac, 4-hydroxythiobenzamide (TBZ) and [2-(2,6-dichloro-phenylamino)-phenyl]-acetic acid 4-thiocarbamoyl-phenyl ester (Compound XVII).

There were 5 rats in each group. Three hours after administration of the test compounds, the rats were euthanized and the extent of gastric hemorrhagic damage was blindly measured (in mm). A "gastric damage score" was produced by summing the lengths of all lesions in a stomach. With reference first to FIG. 8, no gastric damage was seen in the "vehicle" or "Compound XVII" groups. Compound XVII elicited significantly less gastric damage than diclofenac. Moreover, a gastric-sparing effect was not observed if the NSAID moiety (diclofenac) and TBZ were administered separately, but at the same time.

These observations were confirmed by subsequent, blind histological assessment. Samples (100-200) of gastric tissue were excised for measurement of prostaglandin $E_2$ ($PGE_2$) synthesis, as described in detail previously (Wallace et al., Cyclooxygenase 1 contributes to inflammatory responses in rats and mice: implications for gastrointestinal toxicity. *Gastroenterology* 1998; 115: 101-109, incorporated herein by reference). Briefly, the tissue samples were minced with scissors for 30 min, then placed in 1 mL of sodium phosphate buffer (pH 7.4) and placed in a shaking water bath (37° C.) for 20 min. Immediately thereafter, the samples were centrifuged for 1 min at 9,000 g and the supernatant was immediately frozen at −80° C. for subsequent measurement of $PGE_2$ concentration using a specific ELISA (Wallace et al., 1998).

Figure 9:
FIG. 9 illustrates the amount of gastric prostaglandin $E_2$ ($PGE_2$) produced in rats treated with vehicle, diclofenac, 4-hydroxythiobenzamide (TBZ) and [2-(2,6-dichloro-phenylamino)-phenyl]-acetic acid 4-thiocarbamoyl-phenyl ester (Compound XVII).

With reference to FIG. 9, it can be seen that diclofenac (with or without concomitant administration of TBZ) and Compound XVII significantly reduced the amount of gastric $PGE_2$ synthesis, indicating inhibition of COX-1 and/or COX-2. TBZ alone did not reduce gastric $PGE_2$ synthesis when compared to vehicle. Thus, the lack of gastric damage in rats treated with Compound XVII as shown in FIG. 1 was not attributable to an alteration in the ability of these drugs to suppress gastric prostaglandin synthesis. Suppression of gastric $PGE_2$ synthesis was near-complete with these drugs, and with an equimolar dose of diclofenac.

Figure 10:
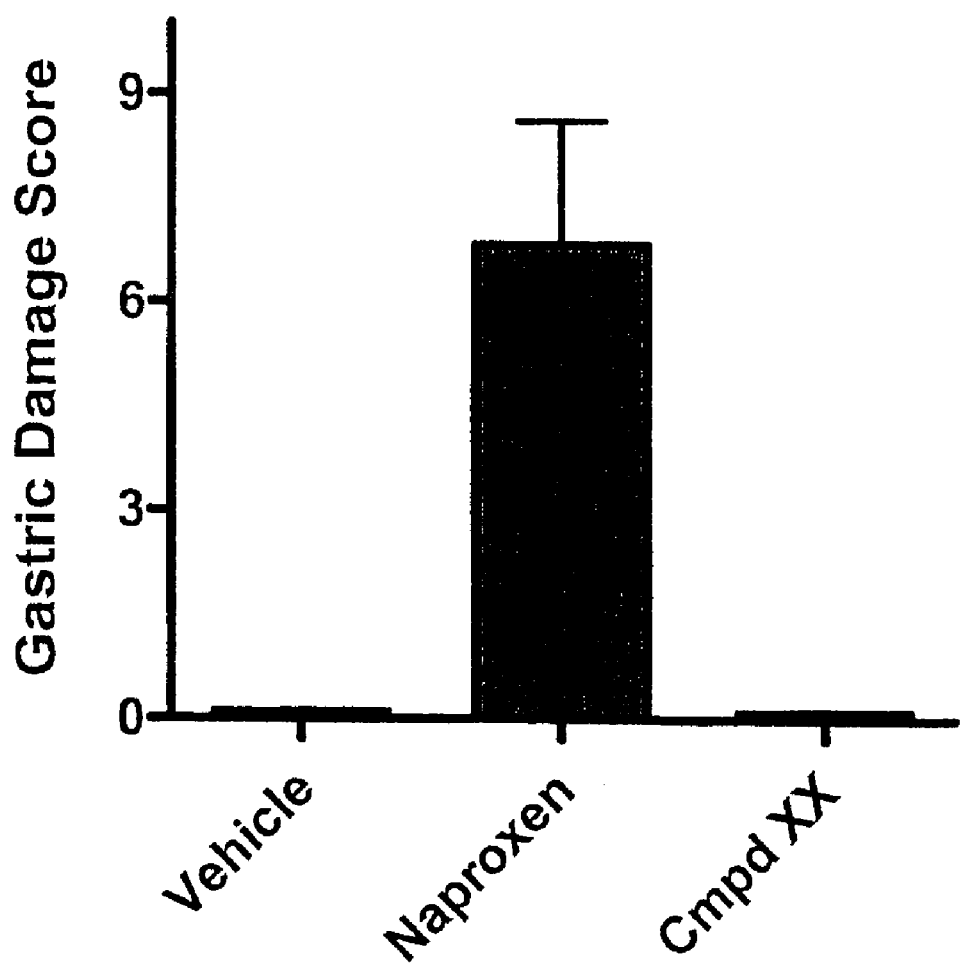
FIG. 10 illustrates the gastric damage score measured in rats treated with vehicle, naproxen, and 2-(6-methoxy-naphthalen-2-yl)-propionic acid 4-thiocarbamyl-phenyl ester (Compound XX).

FIG. 10 shows that the naproxen derivative of the present invention, 2-(6-Methoxy-naphthalen-2-yl)-propionic acid 4-thiocarbamyl-phenyl ester (Compound XX), elicited significantly less damage than naproxen itself. These experiment were performed in exactly the same manner as those shown in FIG. 8. Naproxen and Compound XX were each administered orally at a dose of 60 μmol/kg, and gastric damage was blindly evaluated 3 hours later. Gastric damage was not detectable in any of the rats treated with Compound XX. Each group consisted of 5 rats. These observations were confirmed by subsequent, blind histological assessment.

Figure 11:
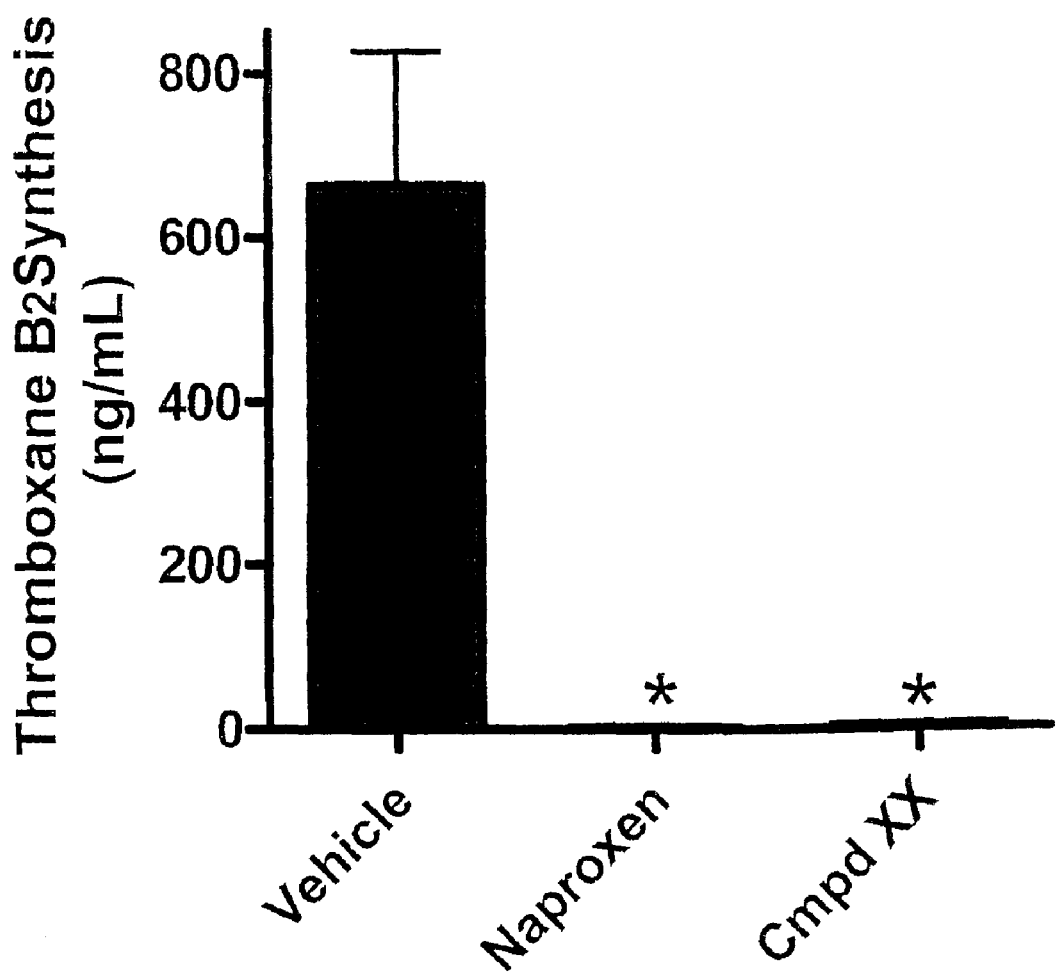
FIG. 11 illustrates the amount of thromboxane $B_2$ synthesis in blood of the rats of FIG. 10.

Inhibition of COX-1 was also measured using the same rats. Immediately after collecting the exudates from the pouch, 1 mL of blood was drawn from the inferior vena cava of each rat and was placed in a glass tube and allowed to clot for 45 min, as described previously (Wallace et al., *Gastroenterology* 1998). The samples were then centrifuged for 3 min at 9,000 g and the supernatant was frozen at −80° C. for subsequent measurement of thromboxane $B_2$ concentrations using a specific ELISA. As shown in FIG. 11, naproxen and Compound XX each significantly ($*p<0.05$) inhibited COX-1 activity as compared to the vehicle-treated group.

Example 18

Inhibition of Cyclooxygenase-2 (COX-2) and Cyclooxygenase-1 (COX-1) by [2-(2,6-dichoro-phenylamino)-phenyl]-acetic acid 4-thiocarbamoyl-phenyl ester Inhibition of COX-2 in vivo was determined using a modified version of a previously described model (Wallace et al., Limited anti-inflammatory efficacy of cyclo-oxygenase-2 inhibition in carrageenan-airpouch inflammation. *Br J Pharmacol* 1999; 126:1200-1204, incorporated herein by reference). Briefly, a subcutaneous "pouch" is created by repeated injections of air over several days. Once established, inflammation in the pouch can be induced by injection of 1 mL of 1% zymosan. This induces a large increase in prostaglandin $E_2$ ($PGE_2$) within the pouch, which has been shown to be derived almost exclusively from COX-2. Groups of 5 rats each were orally treated, 30 min before the carrageenan injection, with vehicle (1% carboxymethylcellulose), diclofenac (3 mg/kg) or [2-(2,6-dichloro-phenylamino)-phenyl]-acetic acid 4-thiocarbamoyl-phenyl ester Compound XVII (4.1 mg/kg). Another group of 5 rats was treated with the vehicle, but received an injection of 0.9% sterile saline into the pouch rather than zymosan.

Figure 12:
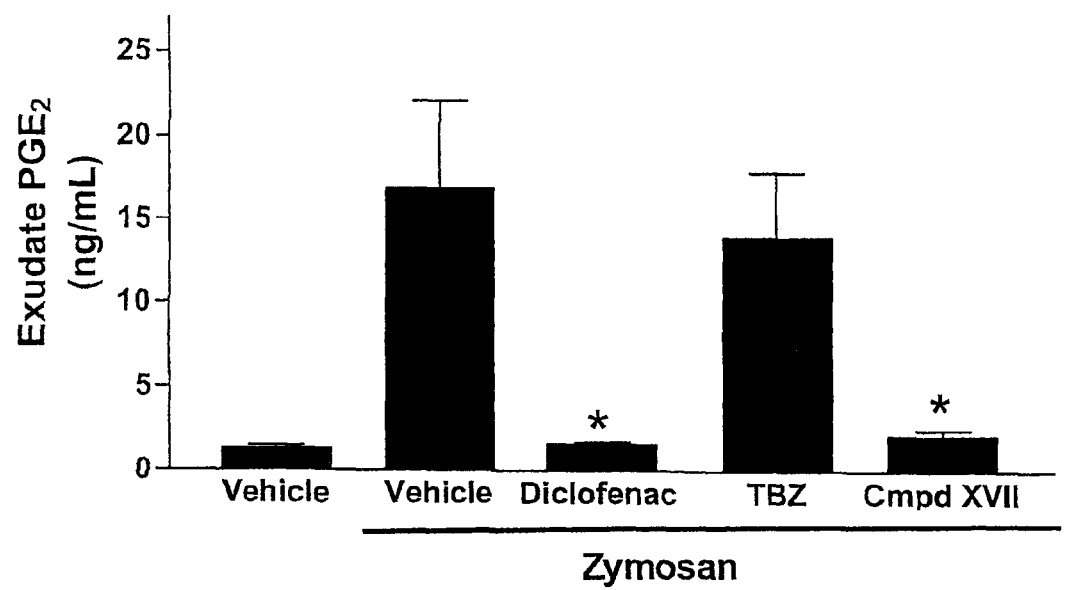
FIG. 12 illustrates the amount of exudate $PGE_2$ produced in the subcutaneous pouch of rats using the rat airpouch assay when treated with vehicle, diclofenac, and [2-(2,6-dichloro-phenylamino)-phenyl]-acetic acid 4-thiocarbamoyl-phenyl ester (Compound XVII).

As can be seen in FIG. 12, pretreatment with either diclofenac or Compound XVII markedly reduced the concentrations of $PGE_2$ within the pouch that were produced in response to injection of zymosan. $*p<0.05$ versus the group treated with vehicle+zymosan. These results indicate that both compounds significantly inhibited COX-2. In contrast, TBZ alone did not significantly affect COX-2 activity.

Figure 13:
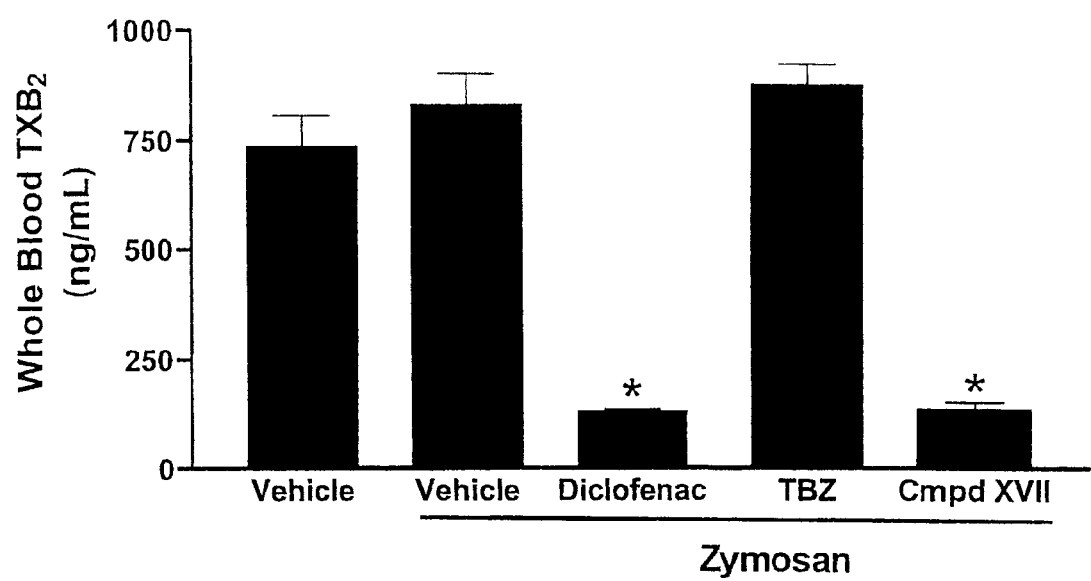
FIG. 13 illustrates the amount of whole blood thromboxane $B_2$ ($TXB_2$) in the rats of FIG. 12.

Inhibition of COX-1 was also measured using the same rats, using the same method as described for FIG. 11. As shown in FIG. 13, diclofenac and Compound XVII each inhibited whole blood thromboxane synthesis, which occurs via COX-1, by greater than 80%. In contrast, TBZ did not significantly affect COX-1 activity.

Example 19

Effects of NSAID Derivatives on Gastric Damage, COX-1 and COX-2 Activity In Vivo The anti-inflammatory effects (COX-2 and COX-1 inhibition) and gastric safety of a number of compounds were compared using the assays described above. The results are summarized in Table 1. All of the parent NSAIDs caused significant gastric damage. However, the TBZ derivatives of the present invention showed improved gastric safety as compared to the parent drugs. It can also be seen from Table 1 that the TBZ derivatives either maintained or actually increased their ability to inhibit COX-1 and/or COX-2 when compared to the parent drug.

TABLE 1

Effects of NSAID Derivatives on Gastric Damage, COX-1 and COX-2 Activity In Vivo

| Compound | NSAID Moiety | Dose (μmol/kg) | Gastric Damage | Inhibition of COX-1 | Inhibition of COX-2 |
|---|---|---|---|---|---|
| XVII | Diclofenac | 30 | ↓ | ↔ | ↔ |
| XX | Naproxen | 60 | ↓ | ↔ | ↑ |
| XIX | Indomethacin | 30 | ↓ | ↑ | ↔ |

Definitions
↑: statistically significant increase versus the parent drug (p < 0.05)
↓: statistically significant decrease versus the parent drug (p < 0.05)
↔: no significant change versus the parent drug Example 20

Effect of NSAID Derivatives on Inflammation

The anti-inflammatory effects of [2-(2,6-dichloro-phenylamino)-phenyl]-acetic acid 4-thiocarbamoyl-phenyl ester (Compound XVII) with those of diclofenac were evaluated using the carrageenan hindpaw edema model as previously described in Wallace et al., *Gastroenterology* 1998. Male, Wistar rats weighing 175-200 g were given the test compounds orally 30 min prior to subplantar injection of 100 ul of 1% lambda carrageenan. Paw volume measured using an Ugo Basile hydroplethysmometer prior to carrageenan injection and at 1-h intervals thereafter for 5 h. Each group, which consisted of 5 rats, were treated with diclofenac at doses of 1, 3 or 10 mg/kg or with Compound XVII at doses equimolar to diclofenac at 3 mg/kg.

Figure 14:
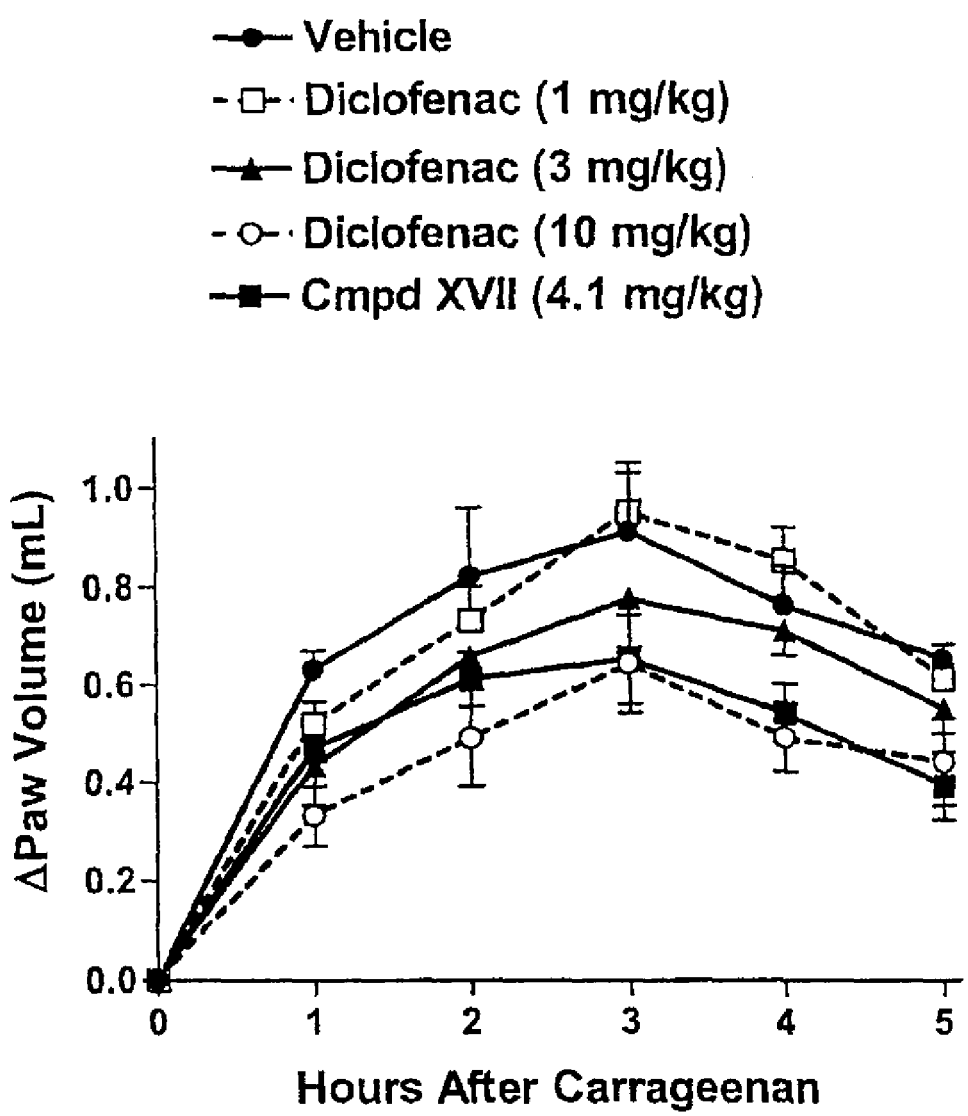
FIG. 14 illustrates the inhibition of paw volume increase in rats treated with vehicle, diclofenac and [2-(2,6-dichloro-phenylamino)-phenyl]-acetic acid 4-thiocarbamoyl-phenyl ester (Compound XVII).

As shown in FIG. 14, diclofenac dose-dependently reduced paw edema induced by subplantar injection of carrageenan. Compound XVII, given at a dose equimolar to diclofenac at 3 mg/kg, reduced paw edema to a greater extent. Indeed, the effect of Compound XVII on paw edema was comparable to the effect of diclofenac at a dose of 10 mg/kg.

Because Compound XVII suppresses prostaglandin synthesis to the same extent as diclofenac, the enhanced activity of the new compounds of the invention in the paw edema model is most likely related to another attribute of the compound. It has previously been demonstrated that hydrogen sulfide donors can significantly reduce carrageenan-induced paw edema in the rat (Zanardo et al., Hydrogen sulphide is an endogenous modulator of leukocyte-mediated inflammation. *FASEB J* 2006; 20: 2118-2120, incorporated herein by reference), so, without being bound to theory, it is likely that $H_2S$ release from Compound XVII accounts for the enhanced anti-inflammatory effects in comparison to diclofenac.

Figure 15:
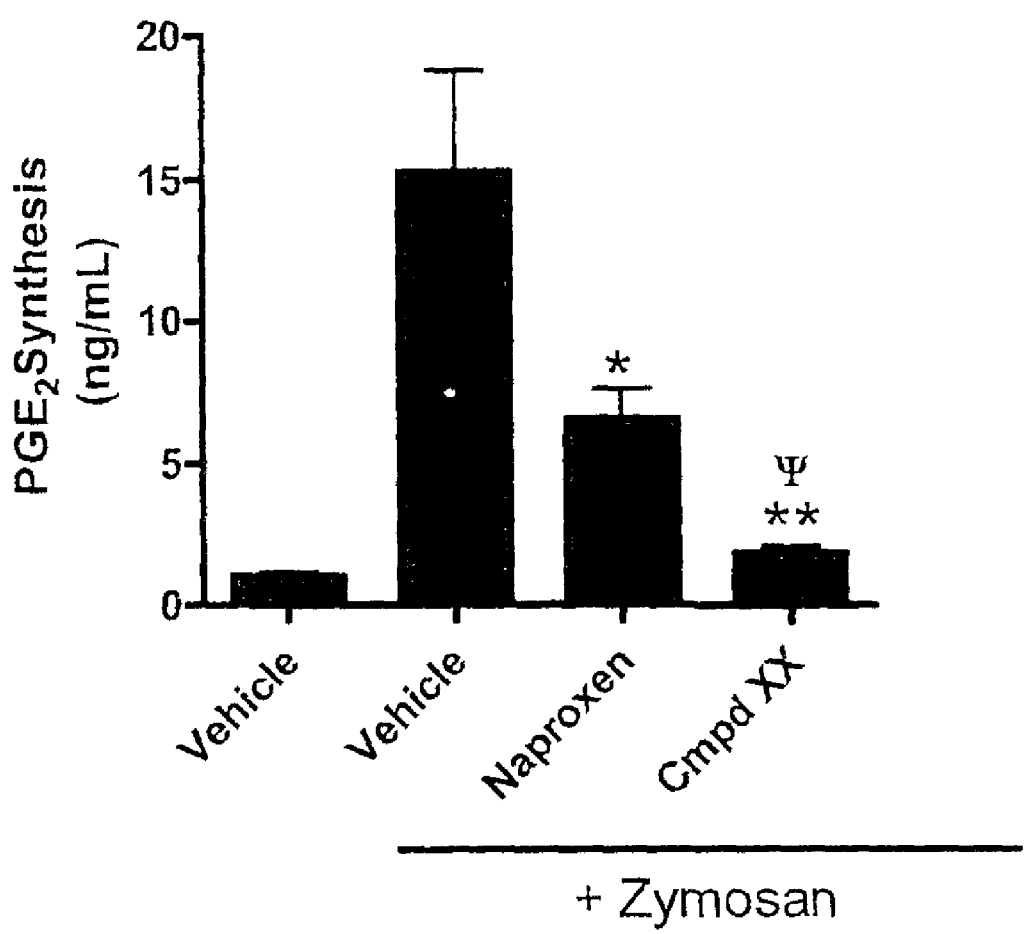
FIG. 15 illustrates the amount of exudate $PGE_2$ produced in the subcutaneous pouch of rats using the rat pouch assay when treated with vehicle, naproxen, and 2-(6-methoxy-naphthalen-2-yl)-propionic acid 4-thiocarbamyl-phenyl ester (Compound XX).

Without being bound to theory, it is also possible that some of the additional activity of the compounds of this invention in models of inflammation may be attributable to enhanced inhibition of COX-2 activity. The effects of vehicle, naproxen and 2-(6-Methoxy-naphthalen-2-yl)-propionic acid 4-thiocarbamyl-phenyl ester (Compound XX) were compared in the rat airpouch model (as described for FIG. 12). Each group consisted of 5 rats. Naproxen and Compound XX were each administered at a dose of 60 µmol/kg. As shown in FIG. 15, both naproxen and Compound XX significantly suppressed COX-2 activity as compared to the group treated with vehicle (*$p<0.05$, **$p<0.01$).

Figure 16:
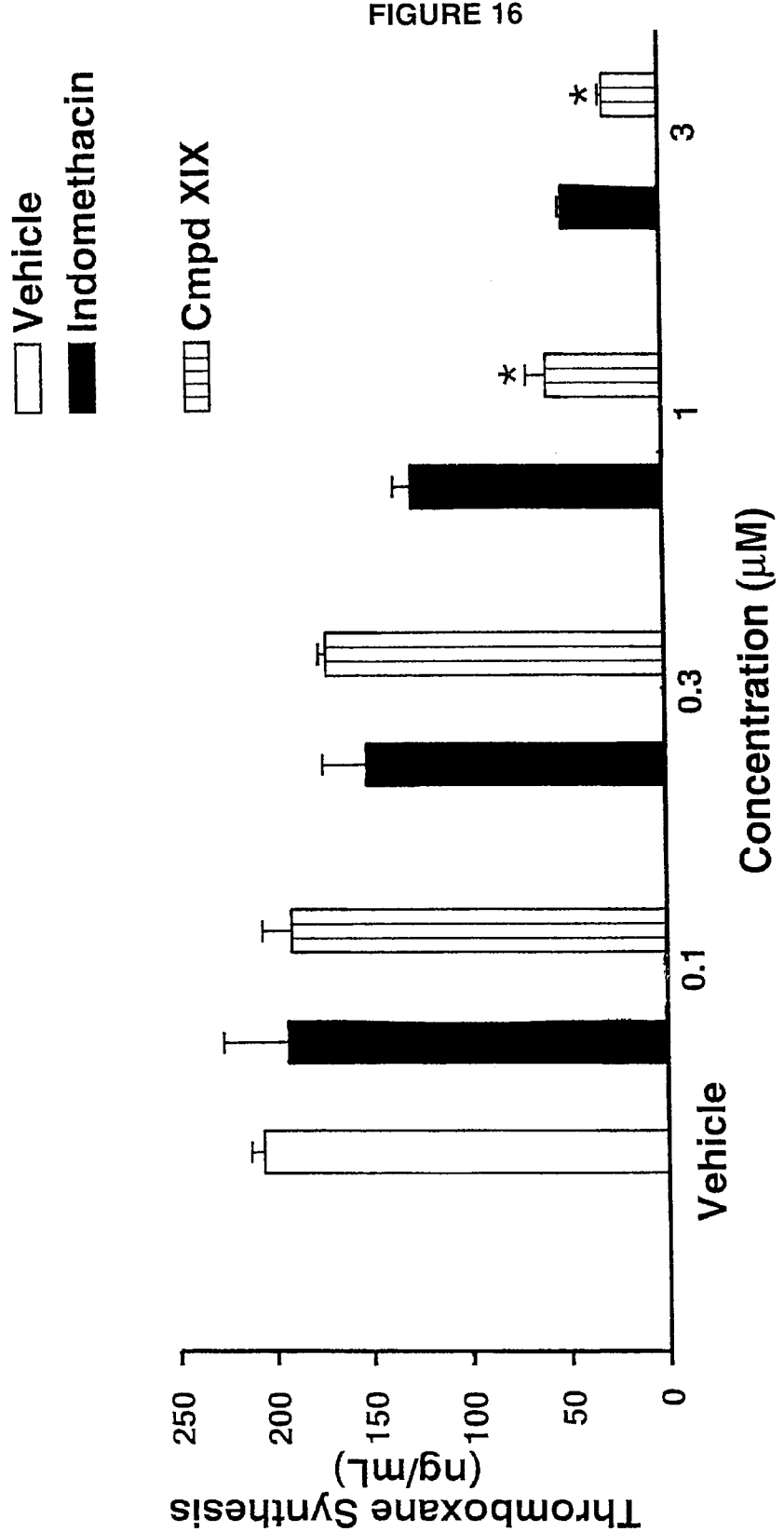
FIG. 16 illustrates thromboxane synthesis (ng/mL) by human blood (in vitro) as a function of concentration of indomethacin and [1-(4-Chloro-benzoyl)-5-methoxy-2-methyl-1-H-indol-3-yl]-acetic acid 4-thiocarbamoyl-phenyl ester (Compound XIX).

Without being bound to theory, it is also possible that some of the additional activity of the NSAID derivatives of this invention in models of inflammation may be attributable to enhanced inhibition of COX-1 activity. The effects of vehicle, indomethacin and [1-(4-Chloro-benzoyl)-5-methoxy-2-methyl-1-H-indol-3-yl]-acetic acid 4-thiocarbamoyl-phenyl ester (Compound XIX), were compared for their effects on human whole blood thromboxane $B_2$ synthesis in vitro. Aliquots (0.5 mL) of blood from healthy human volunteers were added to glass tubes containing 10 uL of methanol alone, or one of the test drugs prepared such that the final concentration would be 0.1, 0.3, 1 or 3 µM. The tubes were placed in water bath (37° C.) with gentle shaking for 45 min, after which they were centrifuged (1,000×g) for 10 minutes. The concentration of thromboxane $B_2$ in each sample was then determined using a specific ELISA, as in the studies shown in FIG. 11. As shown in FIG. 16, both indomethacin and Compound XIX produced a concentration-dependent inhibition of COX-1 activity as compared to the vehicle-treated group. However, at concentrations of 1 and 3 µM, Compound XIX, produced a significantly greater (*$p<0.05$) inhibition of COX-1 activity than that produced by indomethacin.

Example 21

Leukocyte Adherence to the Vascular Endothelium of NSAID Derivatives of the Present Invention Leukocyte adherence to the vascular endothelium is an early event in inflammatory reactions and contributes to thrombus formation. Hydrogen sulfide donors have been shown to reduce leukocyte adherence induced by aspirin or by the pro-inflammatory tripeptide, fMLP (Zanardo et al., *FASEB J* 2006; 20: 2118-2120). The effects of several derivatives of NSAIDs of the present invention on leukocyte adherence were evaluated using intravital microscopy in the rat, as described in detail by Zanardo et al. *FASEB J* 2006; 20: 2118-2120.

Briefly, post-capillary mesenteric venules in anestheitized rats are examined under a light microscope. After a basal recording period of 5 min, one of the test compounds listed in Table 2 below was administered intragastrically at a dose of 30 µmol/kg, with the exception of naproxen and 2-(6-Methoxy-naphthalen-2-yl)-propionic acid 4-thiocarbamyl-phenyl ester (Compound XX), which were administered at a dose of 60 µmol/kg. All test compounds were prepared in a vehicle of 1% carboxymethylcellulose. Changes in leukocyte adherence within the venule were recorded with a video camera attached to the microscope, and quantification of the numbers of adherent leukocytes was performed in a blind manner through evaluation of the videotaped images. Each group consisted of 5 male, Wistar rats weighing 150-175 g. A leukocyte was considered "adherent" if it remained stationary for 30 seconds or more (results below are expressed as the mean±SEM). At the end of the experiment the stomach was opened and examined for the presence of gastric damage, under a dissecting microscope.

TABLE 2

Leukocyte Adherence to the Vascular Endothelium

| Compound Tested | Number of Adherent Leukocytes (per 100 µm vessel length) | Percent Incidence of Gastric Damage |
| --- | --- | --- |
| Vehicle (1%) | 2.0 ± 0.2 | 0 |
| Aspirin | 7.1 ± 0.4* | 80 |
| Compound XVI | 2.3 ± 0.3 | 0 |
| Diclofenac | 8.6 ± 0.6* | 100 |
| Compound XVII | 2.8 ± 0.5 | 20 |
| Lumiracoxib | 9.3 ± 1.0* | 0 |
| Compound XVIII | 2.3 ± 0.4 | 0 |
| Indomethacin | 14.4 ± 0.7* | 100 |
| Compound XIX | 3.0 ± 0.4 | 0 |
| Naproxen | 10.2 ± 0.4* | 100 |
| Compound XX | 2.3 ± 0.5 | 0 |

*$p < 0.05$ versus the vehicle-treated group (ANOVA and Dunnett's Multiple Comparison Test).

It can be seen from Table 2 that the TBZ derivative of aspirin, Compound XVI, of the present invention, significantly reduced the number of adherent leukocytes per 100 µm vessel length when compared to aspirin alone. In addition, Compound XVI significantly reduced the percent incidence of gastric damage when compared to aspirin alone. Similarly, Table 2 further shows that the TBZ derivative of diclofenac, Compound XVII, of the present invention, significantly reduced the number of adherent leukocytes per 100 µm vessel length and significantly reduced the percent incidence of gastric damage when compared to diclofenac alone. Likewise, Table 2 further shows that the TBZ derivative of naproxen, Compound XX, of the present invention, significantly reduced the number of adherent leukocytes per 100 µm vessel length and significantly reduced the percent incidence of gastric damage when compared to naproxen alone.

Interestingly, the TBZ derivative of lumiracoxib, a COX-2 selective inhibitor having reduced gastric side effect, Compound XVIII, still showed no incidences of gastric damage but significantly reduced the number of adherent leukocytes per 100 µm vessel length when compared to lumiracoxib alone. Thus, covalently linking TBZ to COX-2 selective NSAIDs might reduce the cardiovascular side effects of these COX-2 inhibitors as well.

Thus, the NSAID derivatives of the present invention may result in reduced cardiovascular side effects of the NSAID by reducing leukocyte adherence.

Example 22

Effects of NSAID Derivatives of the Present Invention on Gastric Ulcer Healing

Figure 17:
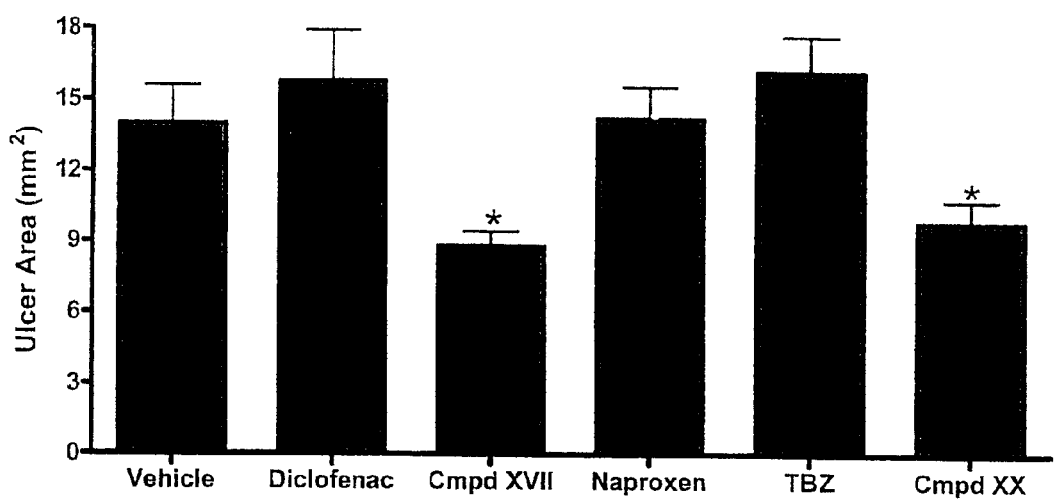
FIG. 17 illustrates the surface area, in $mm^2$, of gastric ulcers in the rat following daily treatment for one week with vehicle, diclofenac, 2-(6-methoxy-naphthalen-2-yl)-propionic acid 4-thiocarbamyl-phenyl ester (Compound XVII), naproxen and 2-(6-methoxy-naphthalen-2-yl)-propionic acid 4-thiocarbamyl-phenyl ester (Compound XX).

NSAIDs, including those selective for COX-2, often inhibit healing of pre-existing gastric ulcers (Stadler et al., *Diclofenac delays healing of gastroduodenal mucosal lesions. Double-blind, placebo-controlled endoscopic study in healthy volunteers*. Digestive Diseases and Sciences 1991; 36: 594-600). To determine the effects of two compounds of the present invention (Compound XVII and Compound XX), as compared to diclofenac and naproxen, respectively, on ulcer healing, rats were treated with these drugs after ulcers had been induced in their stomachs. Gastric ulcers were induced via serosal application of acetic acid, as described by Elliott et al., *A nitric oxide-releasing nonsteroidal anti-inflammatory drug accelerates gastric ulcer healing in rats*. Gastroenterology 1995; 109: 524-530. Beginning three days later, groups of 5 rats each were treated twice-daily, orally, with vehicle, diclofenac, (30 μmol/kg), Compound XVII (30 μmol/kg), naproxen (60 μmol/kg) or Compound XX (60 μmol/kg). After 4 days of such treatment, the rats were euthanized and the stomach was excised and photographed. The area (in $mm^2$) of the ulcer was determined planimetrically by an individual unaware of the treatments given to the rats. In a subgroup of 5 rats euthanized 3 days after induction of gastric ulcers (i.e., prior to initiation of drug treatment), the mean surface area of the ulcers was 24±2 $mm^2$. As illustrated in FIG. 17, rats treated with vehicle, diclofenac or naproxen exhibited similar degrees of healing. However, rats treated with Compound XVII or Compound XX exhibited significantly greater healing (*$p<0.05$ compared to diclofenac and naproxen, respectively). Treatment with TBZ alone did not significantly affect the healing of gastric ulcers as compared to the vehicle-treated group.

Example 23

Effects of NSAID Derivatives of the Present Invention on Blood Pressure

Figure 18:
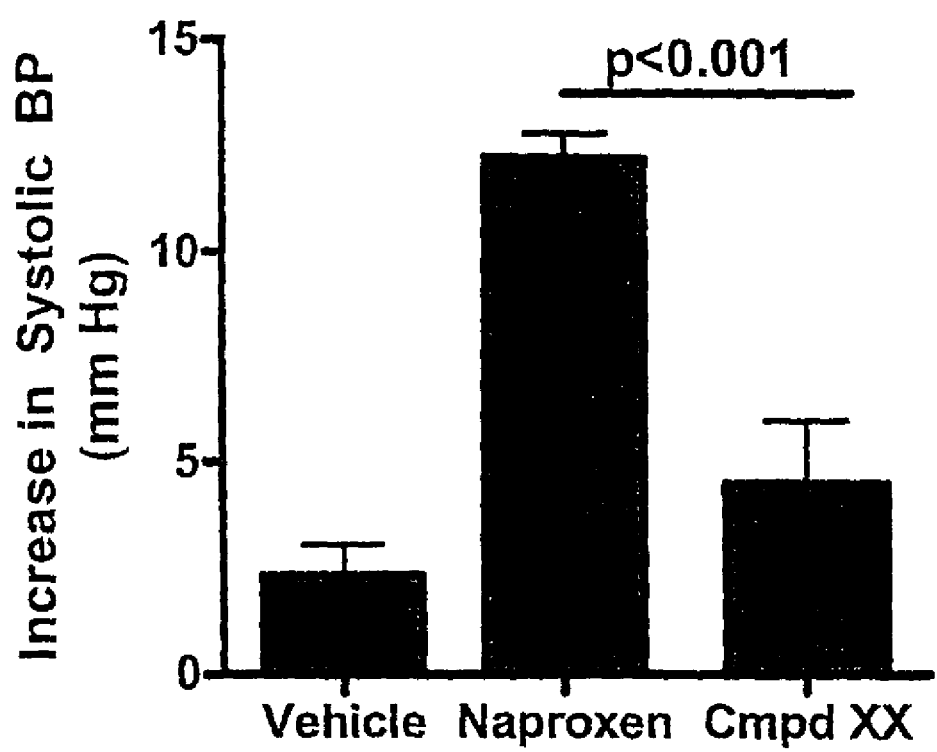
FIG. 18 illustrates the increase in systolic blood pressure (mm Hg) in rats treated with vehicle, naproxen and 2-(6-methoxy-naphthalen-2-yl)-propionic acid 4-thiocarbamyl-phenyl ester (Compound XX).

NSAIDs, including those exhibiting selectivity for COX-2, may exacerbate pre-existing hypertension and interfere with the effectiveness of some anti-hypertensive medications (Whelton, A. *Nephrotoxicity of nonsteroidal anti-inflammatory drugs: physiologic foundations and clinical implications*. Am. J. Med. 1999; 106 (5B): 13S-24S). To determine the effects of the naproxen derivative of the present invention, Compound XX, as compared to naproxen alone, on blood pressure, rats given these drugs intraperitoneally after first inducing hypertension. The rats were provided with drinking water supplemented with Nω-nitro-L-arginine methylester (400 mg/L) for 7 days prior to the experiment, as described previously by Ribeiro et al. (*Chronic inhibition of nitric oxide synthesis: A new model or arterial hypertension*. Hypertension 1992; 20: 298-303). The rats (5 to 8 per group) were anesthetized with Halothane and a carotid artery was cannulated for measurement of blood pressure, which was recorded continuously on a chart recorder. After measuring a stable blood pressure for at least 15 minutes, either naproxen or Compound XX was injected intraperitoneally as a bolus at 60 μmol/kg. Changes in blood pressure were recorded for 60 minutes after the injection. The mean basal blood pressure was 150±6 mm Hg. FIG. 18 illustrates that naproxen caused a substantial increase in systolic blood pressure. In contrast, Compound XX did not increase systolic blood pressure as compared to the vehicle-treated group, and the change in blood pressure was significantly lower than that induced by diclofenac and naproxen, respectively.

Example 24

Measurement of $H_2S$ Generated with [2-(2,6-dichloro-phenylamino)-phenyl]-acetic acid 4-thiocarbamoyl-phenyl ester To compare the in vitro $H_2S$ release induced by [2-(2,6-dichloro-phenylamino)-phenyl]-acetic acid 4-thiocarbamoyl-phenyl ester, Compound XVII, and TBZ, 100-150 mg of isolated livers were homogenized in 1 ml of ice-cold T-PER protein extractor. Two ml of an assay reaction mixture was introduced in to ice-cold 250 μl of NaOH 0.1 N in a sealed 3-neck reactor. The mixture contained 1 mM Compound XVII or 1 mM TBZ dissolved in PEG and 100 mM potassium phosphate buffer (pH=7.4). Incubations were lead with or without presence of 10% (w/v) liver homogenate and 2 mM pyridoxal 5'-phosphate. A constant stream of nitrogen was passed through the mixture via a gas-inlet capillary. The reactor was maintained at 37° C. and $H_2S$ extraction was started by introducing 1 ml of 10% trichloroacetic acid solution. The stream of nitrogen carried the sulfide acid in another reactor by cooled connector and bubbling in 2 ml of sulfide anti-oxidant buffer (SAOB) solution, consisting of 2 M KOH, 1 M salicylic acid and 0.22 M ascorbic acid at pH 12.8. After 30 minutes the SAOB solution was removed, and the sulfide concentration was measured with a sulfide sensitive electrode (Model 9616 $S^{2-}/Ag^+$ electrode, Orion Research, Beverly, Mass., USA) and expressed as $H_2S$ (Ubuka, 2002; Khan et al., 1980). Reactions were initiated by transferring the tube from ice bath to a 37° C. water bath. The stream of nitrogen carried the sulfide acid in the second reactor containing 2 ml of SAOB as described previously. After incubating at 37° C. for 90 minutes, 1 ml of 50% trichloroacetic acid solution was added to mixture to stop the reaction. The remainder $H_2S$ in the mixture was carried out via nitrogen stream by other 30 minutes of incubation at 37° C. The concentration of sulfide in SAOB solution was measured with a sulfide sensitive electrode as previously described (Ubuka, 2002; Khan et al., 1980).

Figure 19:
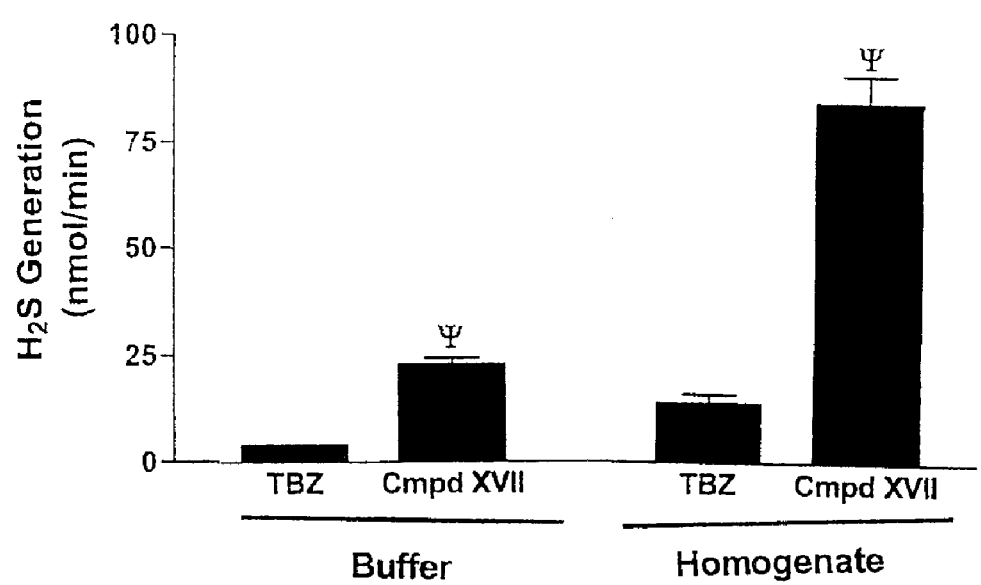
FIG. 19 illustrates the amount of hydrogen sulfide generated from 4-hydroxythiobenzamide (TBZ) and [2-(2,6-dichloro-phenylamino)-phenyl]-acetic acid 4-thiocarbamoyl-phenyl ester (Compound XVII) when incubated in buffer and in liver homogenate.

As shown in FIG. 19, incubation of Compound XVII in buffer resulted in significantly more release of $H_2S$ than an equivalent amount of TBZ. Similarly, there was greater release of $H_2S$ from Compound XVII than from TBZ when incubated with liver homogenate.

Example 25

Effects of Succinic acid 2-{2-[8-(2,2-dimethyl-butyryloxy)-2,6-dimethyl-1,2,6,7,8,8a-hexahydro-naphthalen-1-yl]-ethyl}-6-oxo-tetrahydro-pyran-4-yl ester 4-thiocarbamoyl-phenyl ester (Compound I) and Simvastatin on Human Platelet Aggregation (In Vitro)

Platelet-rich plasma (PRP) was prepared as described in detail previously (Ma L, Elliott S N, Cirino G, Buret A, Ignarro L J, Wallace J L. Platelets modulate gastric ulcer healing through release of endostatin and VEGF. *Proc Natl Acad Sci USA* 98: 6470-6475, incorporated herein by reference). The concentration of platelets in the PRP was adjusted to 1×108 per mL by diluting with Tyrode's buffer (pH 7.4). Aliquots (400 μL) of platelets were placed into a glass cuvette and inserted into a ChronoLog Platelet Aggregometer. Aggregation in response to addition to the cuvette of adenosine diphosphate (ADP) was monitored over a period of 5 min. A concentration-response curve to ADP was first constructed, and then a concentration of ADP producing 70-80% maximal aggregation was used for all subsequent studies. Suspensions of PRP were pre-incubated for 10 min at 37° C. with various concentrations (3-30 μM) of simvastatin or Compound I, or with the vehicle (methanol). The aggregation response to ADP was then assessed. Experiments were repeated 4-6 times for each concentration of each drug.

Figure 20:
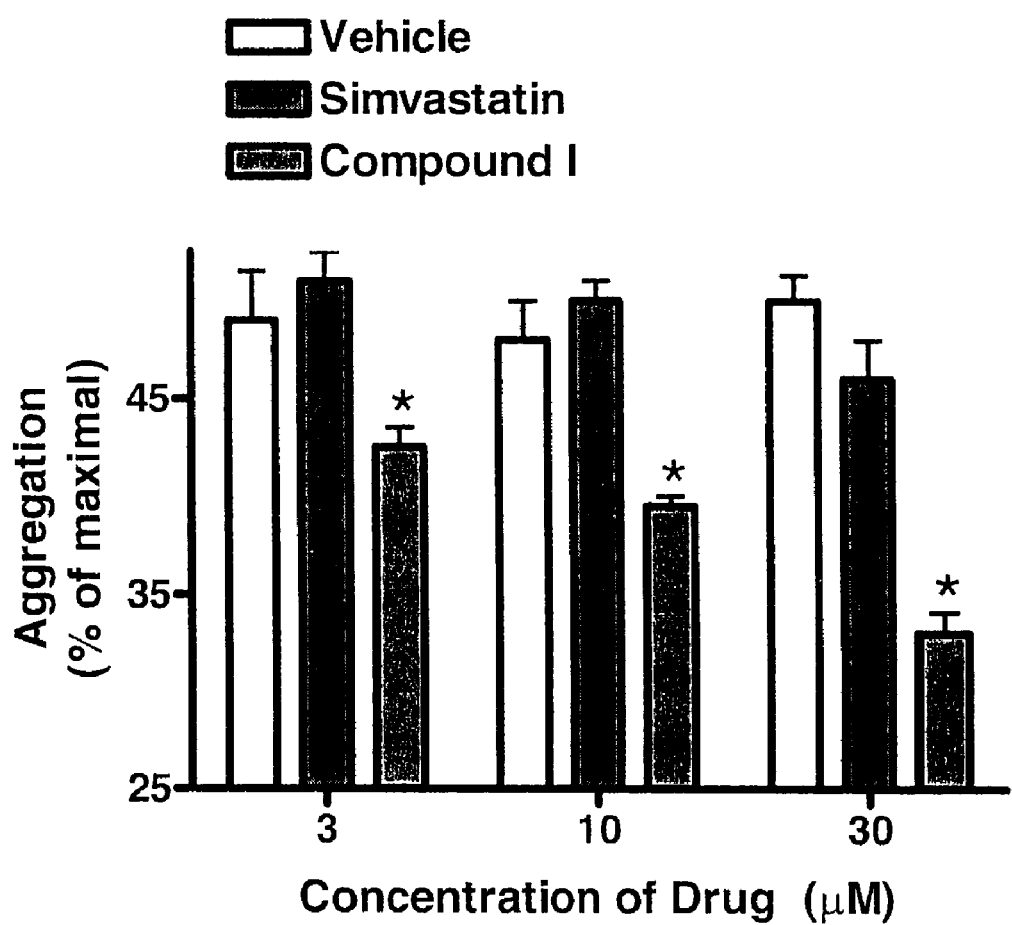
FIG. 20 illustrates the effects of simvastatin and succinic acid 2-{2-[8-(2,2-dimethyl-butyryloxy)-2,6-dimethyl-1,2,6,7,8,8a-hexahydro-naphthalen-1-yl]-ethyl}-6-oxo-tetrahydro-pyran-4-yl ester 4-thiocarbamoyl-phenyl ester (Compound I) on ADP-induced aggregation of human platelets.

FIG. 20 shows the effects of simvastatin and Compound I on ADP-induced aggregation of human platelets. Simvastatin only reduced platelet aggregation at a concentration of 30 μM, while Compound I significantly reduced platelet aggregation at concentrations of 3, 10 and 30 μM (asterisks indicated a significant reduction of platelet aggregation as compared to the corresponding vehicle-treated group; p<0.05).

Example 26

Effects of Compound I and Simvastatin on Human Platelet cAMP (In Vitro)

Platelet-rich plasma (PRP) was prepared as above. Aliquots of 400 μL of PRP were placed in glass tubes which contained IBMX (isobutyl-1-methylxanthine; 0.5 mM), an non-selective phosphodiesterase inhibitor. Two min later, vehicle (methanol) or various concentrations (3-100 μM) of simvastatin or Compound I were added to the tubes. As a positive control, some aliquots of platelets were treated with forskolin (10 μM), a known stimulus of adenylate cyclase. Ten minutes later, the samples of PRP were centrifuged at 9,000 g for 2 min and the supernatant was discarded. The pellet was resuspended in buffer, sonicated for 2 min, then cAMP concentrations were determined using a specific enzyme-linked immunosorbent assay (Cayman Chemical Co., Ann Arbor, Mich., USA). Experiments were repeated 4-6 times for each concentration of each drug.

Figure 21:
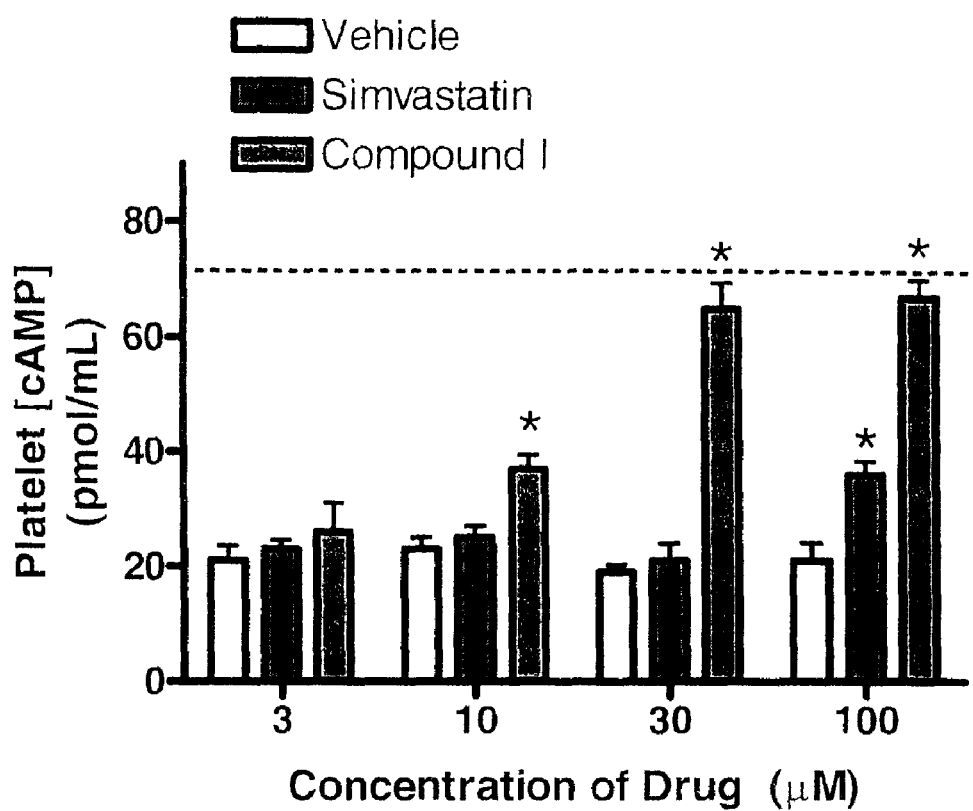
FIG. 21 illustrates the effects of simvastatin and succinic acid 2-{2-[8-(2,2-dimethyl-butyryloxy)-2,6-dimethyl-1,2,6,7,8,8a-hexahydro-naphthalen-1-yl]-ethyl}-6-oxo-tetrahydro-pyran-4-yl ester 4-thiocarbamoyl-phenyl ester (Compound I) on human platelet cAMP concentrations.

FIG. 21 shows the effects of simvastatin and Compound I on human platelet cAMP concentrations. The dotted line indicates the cAMP levels in platelets treated with forskolin (10 μM). Simvastatin only significantly increased platelet cAMP at the highest concentration (100 μM), while Compound I caused a significant increase in platelet cAMP at concentrations of 10, 30 and 100 μM). (asterisks indicated a significant reduction of platelet aggregation as compared to the corresponding vehicle-treated group; p<0.05).

We claim:

1. A compound or its salt having the formula:

A-Y—X        (Formula I)

wherein A is a statin selected from the group consisting of atorvastatin, cilastatin, dermostatin, fluvastatin, lovastatin, mevastatin, pravastatin sodium and simvastatin, Y is

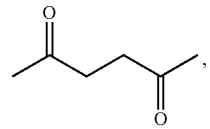

, and X is

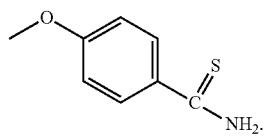

2. The compound according to claim 1, wherein the compound is succinic acid 2-{2-[8-(2,2-dimethyl-butyryloxy)-2,6-dimethyl-1,2,6,7,8,8a-hexahydro-naphthalen-1-yl]ethyl}-6-oxo-tetrahydro-pyran-4-yl ester 4-thiocarbamoyl-phenyl ester.

* * * * *